United States Patent
Bazan et al.

(10) Patent No.: US 10,948,485 B2
(45) Date of Patent: *Mar. 16, 2021

(54) LIGHT HARVESTING MULTICHROMOPHORE COMPOSITIONS AND METHODS OF USING THE SAME

(71) Applicant: THE REGENTS OF THE UNIVERSITY OF CALIFORNIA, Oakland, CA (US)

(72) Inventors: Guillermo C. Bazan, Santa Barbara, CA (US); Brent S. Gaylord, San Diego, CA (US); Shu Wang, Beijing (CN); Bin Liu, Goleta, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/802,327

(22) Filed: Feb. 26, 2020

(65) Prior Publication Data

US 2020/0284785 A1 Sep. 10, 2020

Related U.S. Application Data

(60) Continuation of application No. 16/528,440, filed on Jul. 31, 2019, which is a continuation of application No. 16/152,119, filed on Oct. 4, 2018, which is a continuation of application No. 15/163,525, filed on May 24, 2016, now Pat. No. 10,365,271, which is a continuation of application No. 14/624,466, filed on Feb. 17, 2015, now Pat. No. 10,001,475, which is a continuation-in-part of application No. 13/356,500, filed on Jan. 23, 2012, now Pat. No. 9,371,559, which is a continuation of application No. 11/746,055, filed on May 8, 2007, now Pat. No. 8,101,416, which is a continuation of application No. 10/600,286, filed on Jun. 20, 2003, now Pat. No. 7,214,489, and a continuation-in-part of application No. 14/460,245, filed on Aug. 14, 2014, now Pat. No. 9,085,799, which is a continuation of application No. 14/086,532, filed on Nov. 21, 2013, now Pat. No. 8,841,072, which is a continuation of application No. 13/544,303, filed on Jul. 9, 2012, now Pat. No. 8,617,814, which is a continuation of application No. 12/632,734, filed on Dec. 7, 2009, now Pat. No. 8,227,187, which is a continuation of application No. 11/854,365, filed on Sep. 14, 2007, now Pat. No.

(Continued)

(51) Int. Cl.
| | | |
|---|---|---|
| G01N 33/542 | (2006.01) | |
| G01N 33/58 | (2006.01) | |
| C12Q 1/6818 | (2018.01) | |
| C09B 11/02 | (2006.01) | |
| C09B 69/10 | (2006.01) | |
| C09K 9/02 | (2006.01) | |
| C09K 11/06 | (2006.01) | |
| G01N 33/52 | (2006.01) | |
| B82Y 15/00 | (2011.01) | |

(52) U.S. Cl.
CPC ............ *G01N 33/542* (2013.01); *C09B 11/02* (2013.01); *C09B 69/103* (2013.01); *C09K 9/02* (2013.01); *C09K 11/06* (2013.01); *C12Q 1/6818* (2013.01); *G01N 33/52* (2013.01); *G01N 33/582* (2013.01); *B82Y 15/00* (2013.01); *C09K 2211/1416* (2013.01); *C09K 2211/1425* (2013.01); *C12Q 2565/107* (2013.01)

(58) Field of Classification Search
CPC ... G01N 33/542; G01N 33/582; C12Q 1/6818
See application file for complete search history.

(56) References Cited

U.S. PATENT DOCUMENTS

| | | |
|---|---|---|
| 4,948,843 A | 8/1990 | Roberts et al. |
| 4,950,587 A | 8/1990 | Roberts et al. |

(Continued)

FOREIGN PATENT DOCUMENTS

| | | |
|---|---|---|
| EP | 0708837 | 5/1996 |
| EP | 1281744 | 2/2003 |

(Continued)

OTHER PUBLICATIONS

Ajayaghosh, et at., "A novel approach toward low optical band gap polysquaraines", Organic Letters, 3(16):2595-2598, 2001.

(Continued)

*Primary Examiner* — Jezia Riley
(74) *Attorney, Agent, or Firm* — Bret E. Field; Bozicevic, Field & Francis LLP

(57) ABSTRACT

Light harvesting luminescent multichromophores that are configured upon excitation to transfer energy to, and amplify the emission from, an acceptor signaling chromophore in energy-receiving proximity therewith are provided. Also provided are compositions for labelling a target. The labelling composition may include a donor light harvesting multichromophore and an acceptor signaling chromophore in energy-receiving proximity to the donor light harvesting multichromophore. Also provided is an aqueous composition for labelling a target, including: a donor light harvesting multichromophore; an acceptor signaling chromophore in energy-receiving proximity therewith; and a sensor biomolecule. Methods for using the subject compositions are also provided.

30 Claims, 2 Drawing Sheets

Specification includes a Sequence Listing.

Related U.S. Application Data 7,629,448, which is a division of application No. 10/648,945, filed on Aug. 26, 2003, now Pat. No. 7,270,956, and a continuation-in-part of application No. 10/779,412, filed on Feb. 13, 2004, now Pat. No. 8,993,335, and a continuation-in-part of application No. 13/075,172, filed on Mar. 29, 2011, now Pat. No. 9,159,465, which is a continuation of application No. 11/561,893, filed on Nov. 21, 2006, now Pat. No. 7,914,984, which is a division of application No. 10/666,333, filed on Sep. 17, 2003, now Pat. No. 7,144,950.

(60) Provisional application No. 60/406,266, filed on Aug. 26, 2002, provisional application No. 60/390,524, filed on Jun. 20, 2002, provisional application No. 60/447,860, filed on Feb. 13, 2003.

(56) References Cited

U.S. PATENT DOCUMENTS

| | | |
|---|---|---|
| 5,408,109 A | 4/1995 | Heeger et al. |
| 5,612,221 A | 3/1997 | Simons et al. |
| 5,869,350 A | 2/1999 | Heeger et al. |
| 5,881,083 A | 3/1999 | Diaz-Garcia et al. |
| 5,968,762 A | 10/1999 | Jadamec et al. |
| 5,990,479 A | 11/1999 | Weiss et al. |
| 5,998,135 A | 12/1999 | Rabbani et al. |
| 6,008,373 A | 12/1999 | Waggoner et al. |
| 6,090,552 A | 7/2000 | Nzarenko et al. |
| 6,263,286 B1 | 7/2001 | Gilmanshin et al. |
| 6,268,222 B1 | 7/2001 | Chandler et al. |
| 6,280,933 B1 | 8/2001 | Glazer et al. |
| 6,350,431 B1 | 2/2002 | Snow et al. |
| 6,534,329 B2 | 3/2003 | Heeger et al. |
| 6,545,164 B1 | 4/2003 | Waggoner et al. |
| 6,579,726 B1 | 6/2003 | Natan et al. |
| 6,589,731 B1 | 7/2003 | Chen et al. |
| 6,743,640 B2 | 6/2004 | Whitten et al. |
| 6,808,542 B2 | 10/2004 | Nguyen et al. |
| 6,951,682 B1 | 10/2005 | Zebala |
| 6,979,543 B2 | 12/2005 | Chen et al. |
| 7,122,383 B2 | 10/2006 | Jones et al. |
| 7,141,437 B2 | 11/2006 | Dvornic et al. |
| 7,144,950 B2 | 12/2006 | Bazan et al. |
| 7,208,122 B2 | 4/2007 | Swager et al. |
| 7,214,489 B2 | 5/2007 | Bazan et al. |
| 7,270,956 B2 | 9/2007 | Bazan et al. |
| 7,629,448 B2 | 12/2009 | Bazan et al. |
| 7,666,594 B2 | 2/2010 | Bazan et al. |
| 7,767,405 B2 | 8/2010 | Gillies et al. |
| 7,811,755 B2 | 10/2010 | Bazan et al. |
| 7,897,684 B2 | 3/2011 | Bazan et al. |
| 7,914,984 B2 | 3/2011 | Bazan et al. |
| 8,101,416 B2 | 1/2012 | Bazan et al. |
| 8,158,444 B2 | 4/2012 | Gaylord et al. |
| 8,227,187 B2 | 7/2012 | Bazan et al. |
| 8,993,335 B2 | 3/2015 | Bazan et al. |
| 9,159,465 B2 | 10/2015 | Bazan et al. |
| 9,371,559 B2 | 6/2016 | Bazan |
| 10,001,473 B2 * | 6/2018 | Bazan .................. C09B 69/103 |
| 10,001,475 B2 * | 6/2018 | Bazan .................. C09B 11/02 |
| 10,365,271 B2 * | 7/2019 | Bazan .................. C09K 9/02 |
| 2001/0026921 A1 | 10/2001 | Rabbani et al. |
| 2002/0009728 A1 | 1/2002 | Bittner et al. |
| 2002/0034747 A1 | 3/2002 | Marcel et al. |
| 2002/0150759 A1 | 10/2002 | Jones et al. |
| 2002/0177136 A1 | 11/2002 | McBranch et al. |
| 2003/0054413 A1 | 3/2003 | Kumaraswamy et al. |
| 2003/0087311 A1 | 5/2003 | Wolf |
| 2004/0009506 A1 | 1/2004 | Stephan et al. |
| 2004/0023248 A1 | 2/2004 | O'Malley |
| 2004/0023317 A1 | 2/2004 | Motamedi et al. |
| 2004/0121337 A1 | 6/2004 | Deans et al. |
| 2004/0241768 A1 | 12/2004 | Whitten et al. |
| 2005/0003386 A1 | 1/2005 | Bazan et al. |
| 2005/0064239 A1 | 3/2005 | Take |
| 2005/0064604 A1 | 3/2005 | Bohmann et al. |
| 2005/0196775 A1 | 9/2005 | Swager et al. |
| 2006/0073607 A1 | 4/2006 | Rose et al. |
| 2006/0127929 A1 | 6/2006 | Swager et al. |
| 2006/0175193 A1 | 8/2006 | Inganas et al. |
| 2006/0183140 A1 | 8/2006 | Bazan et al. |
| 2006/0216734 A1 | 9/2006 | Bazan et al. |
| 2006/0216759 A1 | 9/2006 | Naasani |
| 2007/0178470 A1 | 8/2007 | Bissonnette et al. |
| 2008/0038751 A1 | 2/2008 | Asberg et al. |

FOREIGN PATENT DOCUMENTS

| | | | |
|---|---|---|---|
| EP | 0990903 | 3/2003 | |
| EP | 0684239 | 12/2003 | |
| EP | 1279023 | 9/2004 | |
| WO | WO9935288 | 7/1999 | |
| WO | WO-9957222 A1 * | 11/1999 | ............ C08G 61/10 |
| WO | WO0014278 | 3/2000 | |
| WO | WO0066790 | 11/2000 | |
| WO | WO01001144 | 1/2001 | |
| WO | WO01095059 | 12/2001 | |
| WO | WO02081735 | 10/2002 | |
| WO | WO02084271 | 10/2002 | |
| WO | WO03102239 | 12/2003 | |
| WO | WO04001379 | 12/2003 | |
| WO | WO04037886 | 5/2004 | |
| WO | WO04077014 | 9/2004 | |
| WO | WO05056628 | 6/2005 | |
| WO | WO06092063 | 9/2006 | |
| WO | WO07001438 | 1/2007 | |

OTHER PUBLICATIONS

Anissimov, M. "How Many Species of Bacteria are There", (wisegeek.com, accessed Sep. 23, 2011).

Balakin et al., "Conjugates of oligonucleotides with polyaromatic fluorophores as promising DNA probes", Biosensors & Bioelectronics, 1998, 13, 771-778.

Bardea, et al., "Sensing and amplification of oligonucleotide-DNA interactions by means of impedance spectroscopy: a route to a Tay-Sachs sensor", *Chem. Commun.*, 1999, 21-22.

Baur, et al., "Thin-Film Light-Emitting Devices Based on Sequentially Adsorbed Multilayers of Water-Soluble Poly (p-phenylene)s", *Advanced Materials* (1998) 10:17:1452-1455.

Bazan,"Characterisation of tectoRNA Assembly with cationic conjugated polymers", JACS, 126(13):4076-7044, 2004.

Behr, J.P. Synthetic Gene-Transfer Vectors; Ace. *Chem.* Res., 1993, 26: 274-278.

Behr, J.P. DNA Strongly Binds to Micelles and Vesicles Containing Lipopolyamines or Lipointercalants: *Tetrahedron Lett.* (1986) 27:48:5861-5864.

Beier, et al., "Versatile derivatisation of solid support media for covalent bonding on DNA-microchips", Nucleic Acids Research, 1999, 27(9), 1970-1977.

Benson, S.C. et al. Heterodimeric DNA-binding dyes designed for energy transfer: synthesis and spectroscopic properties; *Nucleic Acids Res.* (1993) 21:24:5727-5735.

Betts, et al. A Nucleic Acid Triple Helix Formed by a Peptide Nucleic Acid-DNA Complex; *Science*, 1995, 270:1838-1841.

Bhattacharya, et al., "Interaction of surfactants with DNA. Role of hydrophobicity and surface charge on intercalation and DNA melting", *Biochim.et Biophys. Acta.* (1997) 1323:29-44.

Bhattacharya, et al., "Role of hydrophobic effect and surface charge in surfactant-DNA association", *Indian J. Biochem. & Biophys.* (1997) 34:11-17.

Bier, et at., "Feature-size limitations of microarray technology—a critical review", *Fresenius J. Anal. Chem.*, 2001, 371:151-156.

Birnboim, et al., "Fluorometric Method for Rapid Detection of DNA Strand Breaks in Human White Blood Cells Produced by Low Doses of Radiation", Cancer Res.,1981, 41:1889-1892.

(56) References Cited

OTHER PUBLICATIONS

Blessing, et al., "Monomolecular collapse of plasmid DNA into stable virus-like particles", *Proc. Nat/. Acad. Sci.USA*, 1998, 95:1427-1431.
Brandt, et al., "Peptide nucleic acids on microarrays and other biosensors," TIBS, 22(12):617-622, 2004.
Bronich, et al., "Recognition of DNA Topology in Reactions between Plasmid DNA and Cationic Copolymers", J. Am. Chem. Soc., Sep. 2000, 122(35), 8339-8343.
Cardullo, et al., "Detection of Nucleic Acid Hybridization by Non radiative Fluorescence Resonance Energy Transfer", Proc. Natl. Acad. Sci. USA, Dec. 1998, 85, 8790-8794.
Castro, et al.,"Single-molecule detection of specific nucleic acid sequences in unamplified genomic DNA", *Anal. Chem.* (1997) 69:19:3915-3920.
Chandar, et al. "Fluorescence probe investigation of anionic polymer-cationic surfactant interactions", *Macromolecules* (1988) 21:950-953.
Chehab, et al., "Detection of specific DNA sequences by flu9rescence amplification: A color complementation assay",*Proc. Nat/. Acad. Sci. USA* (1989) 86:9178-9182.
Chen, et al., "A peptide interaction in the major groove of RNA resembles protein interactions in the minor groove of DNA", *Proc. Nat/. Acad. Sci. USA*. (1995) 92:5077-5081.
Chen, et al., "Highly sensitive biological and chemical sensors based on reversible fluorescence quenching in a conjugated polymer" *Proc. Nat/. Acad. Sci. USA*. (1999) 96:22:12287-12292.
Chen, et al. "Using Ethidium Bromide to Probe the Interactions between DNA and Dendrimers", *Langmuir* (2000) 16:15-19.
Chen, et al. "Highly sensitive biological and chemical sensors based on reversible fluorescence quenching in a conjugated polymer", PNAS, 1999, 96(22), 12287-12292.
Chen, et al. "Tuning the Properties of Conjugated Polyelectrolytes through Surfactant Complexation", J. Am. Chern. Soc., 2000, 122, 9302-9303.
Clegg, et al., "Fluorescence Resonance Energy Transfer Analysis of the Structure of the Four-Way DNA Junction", Biochemistry, 1992;31(20):4846-56.
Delling, et al. "The number of positively charged amino acids in the basic domain of Tat is critical for transactivation and complex formation with TAR RNA", *Proc. Nat/. Acad. Sci. USA* (1991) 88:6234-6238.
Demers, et al., "Thermal desorption behavior and binding properties of DNA bases and nucleosides on gold", J Am Chem Soc. 2002;124(38):11248-9.
Demidov, "PNA and LNA throw light on DNA", *Trends in Biotechnology* (2003) 21:1:4-7.
Demidov, et al. "Stability of peptide nucleic acids in human serum and cellular extracts", *Biochem. Phaimacol.* (1994) 48:6:1310-1313.
De Smedt, et al. "Cationic Polymer Based Gene Delivery Systems" *Pharm. Res.* (2000) 17:2:113-126.
Didenko, "DNA Probes Using Fluorescence Resonance Energy Transfer (FRET): Designs and Applications", *Bio Techniques* (2001) 31:5:1106-1121.
Dogariu, et al. Time-resolved Forster energy transfer in polymer blends; *Synthetic Metals* (1999) 100:95-100.
Dore, et al., "Fluorescent Polymeric Transducer for the Rapid, Simple, and Specific Detection of Nucleic Acids at the Zeptomole Level", J. Am. Chern. Soc., 2004, 126, 4240-4244.
Dufourcq, et al. "Molecular assembling of DNA with amphipathic peptides", *FEBS Lett.* (1998) 421:7-11.
Eastman, et al. Biophysical characterization of cationic lipid: DNA complexes; *Biochim. et Biophys. Acta* (1997) 1325:41-62.
Egholm, et al. "PNA hybridizes to complementary oligonucleotides obeying the Watson-Crick hydrogenbonding Rules", *Nature* (1993) 365:566-568.
Egholm, et al. "Recognition of Guanine and Adenine in DNA by Cytosine and Thymine Containing Peptide Nucleic Acids (PNA)", *J. Am. Chern. Soc.* (1992) 114:9677-9678.

Englebienne, P. Synthetic materials capable of reporting biomolecular recognition events by chromic transition; *J. Mater Chern.* (1999) 9:1043-1054.
Epstein, et al., "Microarray technology- enhanced versatility, persistent challenge", Current Opinion in Biotechnology, 2000, 11, 36-41.
Eskilsson, et al. "DNA-Surfactant Complexes at Solid Surfaces", Langmuir (2001) 17:1666-1669.
Felgner, et al. "Nomenclature for Synthetic Gene Delivery Systems", *Hum. Gene Ther.* (1997) 8:511-512.
Ferguson, et al., "Localization of Noncovalently Bound Ethidium in Free and Methionyl-tRNA Synthetase Bound tRNAfMet by Singlet-Singlet Energy Transfer", *Biochemistry* (1986) 25:5298-5304.
Fernandez-Saiz et al. "A Cationic Cyclophane That Forms a Base-Pair Open Complex with RNA Duplexes", *J. Am. Chern. Soc.* (1996) 118:4739-4745.
Frankel,"Peptide models of the Tat-TAR protein-RNA interaction", *Prot. Sci.* (1992) 1:1539-1542.
"Fungi," (Wikipedia.com, accessed Jun. 3, 2013), 31 pages.
Futami, et al. "Optimum Modification for the Highest Cytotoxicity of Cationized Ribonuclease", *J. Biochem.* (2002) 132:223-228.
Gallego, et al., "Targeting RNA with Small-Molecule Drugs: Therapeutic Promise and Chemical Challenges" *Ace. Chern. Res.* (2001) 34:10:836-843.
Gallo, et al., "AIDS in 1988", *Sci. Am.* (1988) 259:4:41-48.
Gallot, et al., "Poly(L-lysine) containing azobenzene units in the side chains: influence of the degree of substitution on liquid crystalline structure and thermotropic behaviour", Liquid Crystals, 1997, 23(1), 137-146.
Ganachaud, et al. "Adsorption of Single-Stranded DNA Fragments onto Cationic Aminated Latex Particles", *Langmuir*(1997) 13:701-707.
Gaylord, "SNP detection using peptide nucleic acid probes and conjugated polymers: Applications in neurodegenerative disease identification", PNAS, 102(1):34-39, 2005.
Gaylord, et al., "Water-Soluble Conjugated Oligomers: Effect of Chain Length and Aggregation on Photoluminescene-Quenching Efficiencies", J. Am. Chern. Soc., 2001, 123, 6417-6418.
Gaylord, et al., "DNA Hybridization Detection with Water-Soluble Conjugated Polymers and Chromophore-Labeled Single-Stranded DNA", J. Am. Chern. Soc., 2003, 125, 896-900.
Gaylord, "DNA detection using water-soluble conjugated polymers and peptide nucleic acid probes", PNAS, 99(17):182, 2002.
Gershon, et al. "Mode of Formation and Structural Features of DNA-Cationic Liposome Complexes Used for Transfection", *Biochemistry* (1993) 32:7143-7151.
Giesen, et al. "A formula for thermal stability ($^T$m) prediction of PNA/DNA duplexes", *Nucleic Acids* Res. (1998) 26:21 :5004-5006.
Glazer, A. N. et al., "Stable Dye-DNA Intercalation Complexes as Reagents for High-Sensitivity Fluorescence Detection," Nature, Oct. 29, 1992, 359, 859-861.
Gossl, et al. "Molecular Structure of Single DNA Complexes with Positively Charged Dendronized Polymers", *J.Am. Chem. Soc.* (2002) 124:6860-6865.
Hage, "Immunoassays", *Anal. Chem.* (1999) 71:12:294R-304R.
Hanvey, et al. "Antisense and Antigene Properties of Peptide Nucleic Acids", *Science* {1992) 258:1481-1485.
Harada, et al., "Chain Length Recognition: Core-Shall Supramolecular Assembly from Oppositely Charged Block Copolymers", *Science* {1999) 283:65-67.
Hawkins, et al., "Incorporation of a fluorescent guanosine analog into oligonucleotides and its application to a real time assay for the HIV-1 integrase 3'-processing reaction", Nucleic Acids Research, 1995, 23(15),2872-2880.
Heeger, et al., "Making Sense of polymer-based biosensors", PNAS, Oct. 1999, 96(22), 12219-12221.
Ho, et al., "Colorimetric and Fluormetric Detection of Nucleic Acids Using Cationic Polythiophene Derivatives", Angew. Chem. Int. Ed., 2002, 41(9), 1548-1551.
Hong, et al., "Water-Soluble Oligmer Dimers Based on Paracyclophane: A New optical Platform for Fluorescent Sensor Applications", J. Am. Chern. Soc., 2002, 124, 11868-11869.

(56) References Cited

OTHER PUBLICATIONS

Huang, et al., "High-Efficiency, Environment-Friendly Electroluminescent Polymers with Stable High Work Function Metal as a Cathode: Green- and Yellow-Emitting Conjugated Polyfluorene Polyelectrolytes and Their Neutral Precursors", J. Am. Chem. Soc., 2004, 126, 9845-9853.
Huang, "Novel Electroluminescent Conjugated Polyelectrolytes based on Polyfluorene", Chemistry of Materials, Am., Chem. Soc., 16(4):708-716, 2004.
Isola, et al. "Surface-Enhanced Raman Gene Probe for HIV Detection", Anal. Chem. (1998) 70:1352-1356.
Izumrudov, et al. "The influence of chain length of a competitive polyanion and nature of monovalent counterions on the direction of the substitution reaction of polyelectrolyte complexes", Makromol. Chem., Rapid Commun. (1988) 9:7-12.
Izumrudov, et al. "Competitive Reactions in Solutions of DNA and Water-Soluble Interpolyelectrolyte Complexes" Biopolymers (1995) 35:523-531.
Izumrudov, et al. "Competitive Displacement of Ethidium Cations Intercalated in DNA by Polycations", Dokl. Phys. Chem. (1995) 342:Nos. 4-6: 150-153.
Izumrudov, et al. "Ethidium Bromide as a Promising Probe for Studying DNA Interaction with Cationic Amphiphiles and Stability of the Resulting Complexes", Langmuir (2002) 18:10348-10356.
Izumrudov, et al. "Controllable Stability of DNA-Containing Polyelectrolyte Complexes in Water-Salt Solutions", Biopolymers. (1999) 52:94-108.
Izumrudov, et al., "Stability of DNA-containing interpolyelectrolyte complexes in watersalt Solutions", Macromol. Chem. Phys. (1999) 200:11 :2533-2540.
Jain, et al., "Rapid Genetic Analysis of RNA-Protein Interactions by Translational Repression in Escherichia coli", Methods Enzymol. (2000) 318:309-332.
Jenkins, et al. "A Sequence-Specific Molecular Light Switch: Tethering of an Oligonucleotide to a Dipyridophenazine Complex of Ruthenium (II)", J. Am. Chem. Soc. (1992) 114:8736-8738.
Johansson, et al. "Intramolecular Dimers: A New Strategy to Fluorescence Quenching in Dual-Labeled Oligonucleotide Probes", J. Am. Chem. Soc. (2002) 124:6950-6956.
Junhui, et al. "DNA Based Biosensors", Biotechnol. Adv. (1997) 15:43-58.
Kabanov, et al. "DNA Interpolyelectrolyte Complexes as a Tool for Efficient Cell Transformation", Biopolymers. (1991) 31:1437-1443.
Kabanov, et al., "DNA Complexes with Polycations for the Delivery of Genetic Material into Cells", Bioconjugate Chem. (1995) 6:7-20.
Kabanov, et al. "Cooperative Interpolyelectrolyte Reactions", Makromol. Chem. Suppl. (1985) 13:137-155.
Karn, et al. "HIV A Practical Approach; RNA binding assays for the regulatory proteins Tat and Rev" IRL Press,New York; (1995) 9:147-165.
Katayose, et al., "Water-Soluble Polyion Complex Associates of DNA and Poly(ethylene glycol)-Poly(L-lysine) Block Copolymer", Bioconjugate Chem. (1997) 8:702-707.
Kircheis, et al. "Tumor targeting with surface-shielded ligand-polycation DNA complexes", J. Controlled Release; (2001) 72:165-170.
Kirsh, et al. "Comparison of Properties of an Oxime-Bound Partially Quaternized Poly-4-Vinylpyridine and a Monomer Analogous Oxime", Eur. Polym. J. (1974) 10:393-399.
Knemeyer, et al, "Probes for detection of specific DNA", Anal. Chem, 72:3717-3724, 2000.
Kwon, et al. "Electrically Erodible polymer gel for controlled release of drugs", Nature (1991) 354:291-293.
Leclerc, "Optical and Electrochemical Transducers Based on Functionalized Conjugated Polymers", Adv. Mater., 1999, 11(18), 1491-1498.
Lee, et al. "ResonSense®: simple linear fluorescent probes for quantitative homogeneous rapid polymerase chain reaction", Anal. Chim. Acta (2002) 457:61-70.
Le-Pecq, et al. "A Fluorescent Complex between Ethidium Bromide and Nucleic Acids", J. Mol Biol. (1967) 27:87-106.

Leulliot, et al., "Current Topics in RNA-Protein Recognition: Control of Specificity and Biological Function through Induced Fit and Conformational Capture", Biochemistry (2001) 40:27:7947-7956.
Life Technologies, Fluorescence SpectraViewer, displaying FITC emission and TAMRA excitation spectra. Datasheet, 2014, 2 Pages.
Lipshutz et al., "High density synthetic oligonucleotide arrays", Nature Genetics Supplement, Jan. 1999, 21, 20-24.
Liu et al., "Blue-light -emitting cationic water-soluble polyfluorene derivatives with tunable quaternization degree", Macromolecules, 35(13):4975-4982, 2002.
Liu, et al., "Homogeneuos Fluorescents-Based DNA Detection with Water-Soluble Conjugated Polymers", Chem. Mater., 2004, 16, 4467-4476.
Liu, et al., "Effect of Chromophore-Charge Distance in the Energy Transfer Properties of Water-Soluble Conjugated Oligomers", J. Am. Chem. Soc., 2003, 125, 6705-6714.
Liu, et al., "Methods for strand-specific DNA detection with cationic conjugation polymers suitable for incorporation into DNA chips and microarrays", PNAS Early Edition, 2004, p. 1-5.
Liu, et al., "Shape-Adaptable Water-Soluble Conjugated Polymers", J. Am. Cham. Soc., 2003, 125, 13306-13307.
Liu, et al., "Interpolyelectrolyte Complexes of Conjugated Copolymers and DNA: Platforms for Multicolor Biosensors", J. Am. Chem. Soc., 2004, 126, 1942-1943.
Lohse, et al., "Fluorescein-Conjugated Lysine Monomers for Solid Phase Synthesis of Fluorescents Peptides and PNA Oligomers", Bioconjugate Chem., 1997, 8, 503-509.
Makino, et al. "Molecular Characterization and Protein Analysis of the cap Region, Which is Essential for Encapsulation in Bacillus anthracis" J. Bacteriol. (1989) 171:2:722-730.
"Mammal," (Wikipedia.com; accessed Sep. 22, 2011), 20 pages.
Manning, G.S. "Thermodynamic Stability Theory for DNA Doughnut Shapes Induced by Charge Neutralization" Biopolymers. (1980) 19:37-59.
Manning, G.S. "The Possibility of Intrinsic Local Curvature in DNA Toroids", Biopolymers. (1981) 20:1261-1270.
Manning, G.S. "The molecular theory of polyelectrolyte solutions with applications to the electrostatic properties of polynucleotides" Qrtly Review of Biophysics. (1978) v.11: 179-246.
Maruyama et al. "Characterization of Interpolyelectrolyte Complexes between Double-Stranded DNA and Polylysine Comb-Type Copolymers Having Hydrophilic Side Chains", Bioconjugate Chem. (1998) 9:292-299.
Matsumoto, et al. "High-Throughput Screening Utilizing Intramolecular Fluorescence Resonance Energy Transfer for the Discovery of the Molecules that Bind HIV-1 TAR RNA Specifically",Bioorg. Med. Chem. Lett. (2000)10:1857-1861.
McLoughlin, et al. "A simple and effective separation and purification procedure for DNA fragments using Dodecyltrimethylammonium bromide", Bioseparation. (2001) 9:307-313.
McQuade, et al., "Conjugated Polymer-Based Chemical Sensors", Chem. Rev., 2000, 100, 2537-2574.
McQuade, et al. "Signal amplification of a "Tum-On" Sensor: Harvesting the Light Captured by a Conjugated Polymer", J. Am. Chem. Soc. (2000) 122:12389-12390.
Mel'Nikov, et al. "Discrete Coil—Globule Transition of Large DNA Induced by Cationic Surfactant", J. Am. Chem. Soc. (1995) 117:2401-2408.
Mergny, et al. "Fluorescence Energy Transfer between Two Triple Helix-Forming Oligonucleotides Bound to Duplex DNA" Biochemistry. (1994) 33:15321-15328.
Miao, et al. "Photophysics of Poly(paracyclophan-1-ene) and Derivatives: Evidence for Intrachain Energy Transfer and Chromophore Aggregation", J. Am. Chem. Soc. (1995) 117:11407-11420.
Miller, I.R. "Interaction of DNA with Heavy Metal Ions and Polybases: Cooperative Phenomena", Biopolymers. (1968) 6:169-179.
Minehan, et al. "Kinetics of DNA Binding to Electrically Conducting Polypyrrole Films", Macromolecules. (1994) 27:777-783.
Morgan, et al., " Native and Denatured DNA, Cross-Linked and Palindromic DNA and Circular CovalenUy-Ciosed DNA Analysed by a Sensitive Fluorometric Procedure", Biochem. Biophys. Res. Commun. (1974) 61:2:396-403.

(56) References Cited

OTHER PUBLICATIONS

"Murinae," (Wikipedia.com, accessed Mar. 18, 2013), 24 pages.
Nguyen, et al. "Nonviral Transfer Technology: Evaluation of polyether-polyethyleneimine graft copolymers as gene transfer agents", *Gene Ther.* (2000) 7:126-138.
Nielsen, P.E. "Applications of peptide nucleic acids", *Analytical biotechnology.* (1999) 10:71-75.
Nilsson, et al., "Chip solution detection of DNA hybridization using a luminescent zwitterionic polythiophene derivative", Nature Materials, Jun. 2003, 2, 419-424 (Supplementary Information pp. 1-2).
Nishanian, et al. "A Simple Method for Improved Assay Demonstrates that HIV p24 Antigen is Present as Immune Complexes in Most Sera from HIV-Infected Individuals", *J. Infect. Dis.* (1990) 162:21-28.
Nuovo, G.J. "In Situ Localization of PCR-Amplified DNA and eDNA", *Methods Mol. Bio.* (2000) 123:217-238.
Olins, et al. "Model Nucleoprotein Complexes: Studies on the Interaction of Cationic Homopolypeptides with DNA" *J. Mol. Bioi.* (1967) 24:157-176.
Pasternack, et al. "Long-Range Fluorescence Quenching of Ethidium Ion by Cationic Porphyrins in the Presence of DNA", *J. Am. Chem. Soc.* (1991) 113:6835-6840.
Patel, et al., "Energy transfer analysis of Fos-Jun dimerization and DNA binding", Proc. Natl. Sci. USA, Jul. 1994, 91, 7360-7364.
Patolsky, et al. "Amplified DNA Detection by Electrogenerated Biochemiluminescence and by the Catalyzed Precipitation of an Insoluble Product on Electrodes in the Presence of the Doxorubicin Intercalator", *Angew. Chem. Int. Ed.* (2002) 41:18:3398-3402.
Patolsky, et al. "Electronic Transduction of DNA Sensing Processes on Surfaces: Amplification of DNA Detection and Analysis of Single-Base Mismatches by Tagged Liposomes", *J. Am Chem. Soc.* (2001) 123:5194-5205.
Peterlinz, et al. "Observation of Hybridization and Dehybridization of Thioi-Tethered DNA using Two-Color Surface Plasmon Resonance Spectroscopy", *J. Am. Chem. Soc.* (1997} 119:3401-3402.
Petty, et al. "Thermodynamic Characterization of the Association of Cyanine Dyes with DNA", *J. Phys. Chern. B.* (2000) 104:7221-7227.
Pilipenko, et al. "A cell cycle-dependent protein serves as a template-specific translation initiation factor", *Genes & Dev.* (2000) 14:2028•2045.
Pinto, et al., "Conjugated Polyelectrolytes: Synthesis and Applications", *Synthesis.* (2002) 9:1293-1309.
Plank, et al. "Branched Cationic Peptides for Gene Delivery: Role of Type and Number of Cationic Residues in Formation and in Vitro Activity of DNA Polyplexes", *Hum. Gene Ther.* (1999} 10:319-332.
"Plant," (Wikipedia.com, accessed Mar. 8, 2013), 15 pages.
Portela, et al., "The influenza virus nucleoprotein: a multifunctional RNA-binding protein pivotal to virus replication", *J. Gen. Virol.* (2002} 83:723-734.
Puglisi, et al. "Conformation of the TAR RNA-Arginine Complex by NMR Spectroscopy", *Science.* (1992) 257:76-80.
Pullman, et al. "Two Aspects of DNA Polymorphism and Microheterogeneity: Molecular Electrostatic Potential and Steric Accesibility", *J. Biochem.* {1982} 124:229-238.
Ranade, et al., "High-Throughput Genotyping with Single Nucleotide Polymorphisms", Genone Research, 2001, 11, 1262-1268.
Raymond, "Detection of target DNA using fluoresence cationic polymer and peptide nucleic acid probes on solid support", BMD Biotechnology, vol. 5, 2005.
Richter, et al. "Specific HIV-1 TAR RNA Loop Sequence and Functional Groups are Required for Human Cyclin T1-Tat-TAR Ternary Complex Formation", *Biochemistry.* (2002) 41:6391-6397.
Saghatelian, et al. "DNA Detection and Signal Amplification via an Engineered Allosteric Enzyme", *J. Am. Chern. Soc.* (2003) 125:344-345.
Saiki, et al. "Enzymatic Amplification of β-Globin Genomic Sequences and Restriction Site Analysis for Diagnosis of Sickle Cell Enemia", *Science.* (1985) 230:1350-1354.
Schork, et al., "Single nucleotide polymorphisms and the future of genetic epidemiology", Clin. Genet., 2000, 58, 250-264.
Service "DNA Analysis: Microchip Arrays Put DNA on the Spot", The American Association for the Advancement of Science, Oct. 1998, 282(5388), 396-399.
Seymour, et al. "Cationic block copolymers as self-assembling vectors for gene delivery; *Self-assembling Complexes for Gene Delivery*", (1998) 11:219-239.
Shinozuka, et al. "A Novel Multifunctionality Labelled DNA Probe Bearing an Intercalator and a Fluorophore", *J.Chem. Soc., Chern. Commun.* (1994) 1377-1378.
Smith, et al., "The synthesis of oligonucleotides containing an aliphatic amino group at the 5' terminus: synthesis of fluorescent DNA primers for use in DNA sequence analysis", Nucleic Acids Research, 1985, 13(7) 2399-2412.
Smith, et al. "Molecular Recognition of PNA-Containing Hybrids: Spontaneous Assembly of Helical Cyanine Dye Aggregates on PNA Templates", *J. Ant Chern. Soc.* (1999) 121:2686-2695.
Smith, et al. "Surfactant structure around DNA in aqueous solution", *Phys. Chern. Chem. Phys.* (2000) 2:1305-1310.
Southern, "DNA chips: analysing sequence by hybridization to oligonucleotides on a large scale", TIG, Mar. 1996, 12(3), 110-115.
Stender, et al. "PNA for rapid microbiology", *J. Microbiological Methods.* (2002) 48:1-17.
Stevens, et al., "Exciton dissociation mechanisms in the polymeric semiconductors poly(9,9-dioctylfluorene) and poly(9,9-dioctylfluorene-co-benzothiadiazole)", Physical Review 8, Apr. 2001, 63, 1-18.
Stewart, "Chromophore-Labeled Dendrons as Light Harvesting Antennae", J. Am. Chern. Soc., 118 (18):4354-4360, 1996.
Stork, et al., "Energy Transfer in Mixtures of Water-Soluble Oligomers: Effect of Charge, Aggregation, and Surfactant Complexation", Adv. Mater., Mar. 2002, 14(5), 361-366.
Su, et al. "Au nanoparticle- and silver-enhancement reaction-amplified microgravimetric biosensor", *Chem. Commun.* (2001) 755-756.
Sullenger, et al., "Emerging clinical applications of RNA", *Nature.* (2002) 418:252-258.
Sun et al., "Application of cationic conjugated polymers in microarrays using label-free DNA targets," Nature Protocols, 2(9):2007.
Takakusa, et al. "Design and Synthesis of an Enzyme-Cleavable Sensor Molecule Jor Phosphodiesterase Activity Based on Fluorescence Resonance Energy Transfer", *J. Am. Chern. Soc.* (2002) 124:8:1653-1657.
Tamilarasu, et al. "A New Strategy for Site-Specific Protein Modification: Analysis of a Tat Peptide—TAR RNA Interaction", *Bioconjugate Chern.* (2001) 12:2:135-138.
Tang, et al., "The influence of polymer structure on the interactions of cationic polymers with DNA and morphology of the resulting complexes" *Gene Ther.* (1997) 4:823-832.
Taton, et al. "Scanometric DNA Array Detection with Nanoparticle Probes", *Science.* (2000) 289:1757-1760.
Taton, et al. "Two-Color Labeling of Oligonucleotide Arrays via Size-Selective Scattering of Nanoparticle Probes", *J. Am. Chem. Soc.* (2001) 123:5164-5165.
Tomac, et al. "Ionic Effects on the Stability and Conformation of Peptide Nucleic Acid Complexes", *J. Am. Chem.Soc.* (1996) 118:5544-5552.
Traser, et al. "Syntheses and solution properties of water-soluble poly(p-phenylene)s bearing oligo( ethylene oxide) and trialkylamino side groups", *e-Polymers.* (2002) 32:1-39.
Umek, et al., "Electronic Detection of Nucleic Acids, a Versatile Platform for Molecular Diagnostics", Journal of Molecular Diagnostics, May 2001, 3(2), 74-84.
Vaishnav, et al., "The Biochemistry of AIDS", *Ann. Rev. Biochem.* (1991) 60:577-630.
Varani, G. "RNA-Protein Intermolecular Recognition" *Ace. Chem. Res.* (1997) 30:5:189-195.
Vehse, et al., "Light Amplification by Optical Excitation of a Chemical Defect in a Conjugated Polymer", Adv. Mater., Jun. 2004, 16(12), 1001-1004.
Vinogradov,et al. "Self-Assembly of Polyamine-Poly( ethylene glycol) Copolymers with Phosphorothioate Oligonucleotides", *Bioconjugate Chem.* (1998) 9:805-812.

(56) References Cited

OTHER PUBLICATIONS

"Virus", (Wikipedia.com, accessed Nov. 24, 2012), 37 pages.
Wang. "Solvent-dependent aggregation of a water-soluble poly (fluorene) controls energy transfer to chromophore-labeled DNA", Chem. Comm, R. Soc. Chem., 2508-2509, 2004.
Wang, et al. "Photoluminescence of Water-Soluble Conjugated Polymers: Origin of Enhanced Quenching by Charge Transfer", *Macromolecules*. (2000) 33:5153-5158.
Wang, "Fluorescein provides a resonance gate for FRET from conjugated polymers to DNA intercalated dyes", JACS, 126(7):5446-5451, 2004.
Wang, et al., "Biosensors from conjugated polyelectrolyte complexes", PNAS, 2002, 99(1), 49-53.
Wang, et al., "Size-Specific Interactions Between Single- and Double-Stranded Oligonucleotides and Cationic Water-Soluble Oligofluorenes", Adv. Funct. Mater., Jun. 2003, 13(6), 463-467.
Wang, "Survey and Summary From DNA biosensors to gene chips", Nucleic Acids Research, 2000, 28(16), 3011-3016.
Wang, et al., "Optically Amplified RNA-Protein Detection Methods Using Light-Harvesting Conjugated Polymers", Adv. Mater., Sep. 2003, 15(17), 1425-1428.
Wang, et al. "DNA Electrochemical Biosensor for the Detection of Short DNA Sequences Related to the Human Immunodeficiency Virus", *Anal. Chem.* (1996) 68:15:2629-2634.
Wang, et al. "Synthesis of AB(BA), ABA and BAB Block Copolymers of tert-Butyl Methacrylate (A) and Ethylene Oxide (B)", *J. Polym. Sci., Part A: Polym. Chem.* (1992) 30:2251-2261.
Wang, et al. "Interaction of DNA with Cationic Micelles: Effects of Micelle Surface Charge Density, Micelle Shape, and Ionic Strength on Complexation and DNA Collapse" *Langmuir*. (2001) 17:1670-1673.
Wang, J. et al., "Dendritic Nucleic Acid Probes for DNA Biosensors," J. Am. Chem. Soc., 1998, 120, 8281-8282.
Waring, M. J. "Complex Formation between Ethidium Bromide and Nucleic Acids", *J. Mol. Bioi.* (1965) 13:269-282.
Weeks, et al. "Fragments of the HIV-1 Tat Protein Specifically Bind TAR RNA", *Science*. (1990) 249:1281-1285.
Weiler et al., "Hybridization Based DNA Screening on Peptide Nucleic Acid (PNA) Oligomer Arrays," Nucleic Acids Research, 1997, 25(14), 2792-2799.
Whitcombe, et al. "Detection of PCR products using self-probing amplicons and fluorescence" *Nat. Biotechnol.* (1999) 17;804-807.
Wintermeyer, et al., "Fluorescent Derivatives of Yeast tRNA(TM)", Eur. J. Biochem., 1979, 98, 465-475.
Wolcott, "Advances in Nucleic Acid-Based Detection Methods", Clinical Microbiology Reviews, Oct. 1992, 5(4), 370-386.
Wolfert, et al. "Polyelectrolyte Vectors for Gene Delivery: Influence of Cationic Polymer on Biophysical Properties of Complexes Formed with DNA", *Bioconjugate* Chem. (1999) 10:993-1004.
Wyman, et al. "Design, Synthesis, and Characterization of a Cationic Peptide that Binds to Nucleic Acids and Permeabilizes Bilayers" *Biochemistry*. (1997) 36:3008-3017.
Xu, et al., "Immobilization and Hybridization of DNA on an Aluminum(III) Alkanebisphosphonate Thin Film with Electrogenerated Chemiluminescent Detection", *J. Am. Chem. Soc.* (1995) 117:2627-2631.
Yang, et al., "Fluorescent Porous Polymer Films as TNT Chemosensors: Etectronic and Structural Effects", *J. Am. Chern. Soc.* (1998) 120:11864-11873.
Zhou, et al., "Methodology for Enhancing the Sensitivity of Fluorescent Chemosensors: Energy Migration in Conjugated Polymers", J. Am. Chem. Soc., 1995, 117, 7017-7018.
Zhou et al., "Fluorescent Chemosensors Based on Energy Migration in Conjugated Polymers: The Molecular Wire Approach to Increased Sensitivity", J. Am. Chem. Soc., 1995, 117, 12593-12602.
International Search Report dated Apr. 14, 2004 in PCT/US2003/019678.
Supplementary EP Search Report dated Sep. 27, 2007 in EP 03761235.5.
Office action dated Oct. 20, 2006 in CN03819836.3.
Office action dated Sep. 25, 2008 in CN03819836.3.
Examination Report dated Jul. 17, 2008 in EP 03761235.5.
First Office Action dated Mar. 17, 2009 in JP 2004-516105.
Examination Report dated Aug. 31, 2006 in NZ 537707.
Written Opinion dated Oct. 7, 2005 and response thereto filed Mar. 6, 2006 in SG 200407571-9.
Examination report dated Jun. 26, 2006 in SG 200407571-9.
International Search Report and Written Opinion dated May 12, 2005 in PCT/US2004/04286.
International Preliminary Report on Patentability dated Aug. 19, 2005 in PCT/US2004/04286.
First Office Action dated Apr. 13, 2007 in CN 200480009631.4.
Supplementary EP Search Report dated Sep. 27, 2007 in EP 04737272.7
International Search Report and Written Opinion dated Dec. 16, 2005 in PCT/US2004/030605.
International Preliminary Report on Patentability dated Mar. 21, 2006 in PCT/US2004/030605.
Examination report dated Sep. 10, 2008 and response thereto filed Mar. 20, 2009 in EP 04821601.4.
International Search Report dated Mar. 18, 2005 in PCT/US2003/026989.
First Office Action dated Apr. 28, 2005 in CN 03824651.1.
Decision on Rejection dated Jul. 6, 2007 in CN 03824651.1.
Request for Reexamination filed Oct. 18, 2007 in CN 03824651.1.
Supplementary European Search Report dated Sep. 20, 2007 in EP 03816297.
Official Action dated Jul. 17, 2008 in EP 03816297.
International Search Report and Written Opinion dated Dec. 12, 2006 in PCT/US2006/00928.
International Preliminary Report on Patentability dated Jul. 10, 2007 in PCT/US2006/00928.
International Search Report and Written Opinion dated Aug. 16, 2006 in PCT/US2006/00882.
International Preliminary Report on Patentability dated Jul. 10, 2007 in PCT/US2006/00882.
International Search Report and Written Opinion dated Sep. 11, 2006 in PCT/US2006/003498.
International Preliminary Report on Patentability dated Jul. 31, 2007 in PCT/US2006/003498.
Examination Report dated Jan. 17, 2008 and response thereto filed Jul. 25, 2008 in EP 04737272.7.

* cited by examiner

SEQUENCE LISTING

<160> NUMBER OF SEQ ID NOS: 10

<210> SEQ ID NO 1
<211> LENGTH: 15

<212> TYPE: DNA
<213> ORGANISM: Artificial Sequence
<220> FEATURE:
<223> OTHER INFORMATION: Synthetic polynucleotide

<400> SEQUENCE: 1
cgtatcactg gactg                                                    15

<210> SEQ ID NO 2
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 2
actgacgata gactg                                                    15

<210> SEQ ID NO 3
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 3
gtaaatggtg ttagggttgc                                               20

<210> SEQ ID NO 4
<211> LENGTH: 40
<212> TYPE: DNA
<213> ORGANISM: Artificial Sequence
<220> FEATURE:
<223> OTHER INFORMATION: Synthetic polynucleotide

<400> SEQUENCE: 4
catctgtaaa tccaagagta gcaaccctaa caccatttac                         40

<210> SEQ ID NO 5
<211> LENGTH: 40
<212> TYPE: DNA
<213> ORGANISM: Artificial Sequence
<220> FEATURE:
<223> OTHER INFORMATION: Synthetic polynucleotide

<400> SEQUENCE: 5
aaaatattgt gtatcaaaat gtaaatggtg ttagggttgc                         40

<210> SEQ ID NO 6
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 6
atcttgacta tgtgggtgct                                               20

<210> SEQ ID NO 7
<211> LENGTH: 20
<212> TYPE: DNA
<213> ORGANISM: Artificial Sequence
<220> FEATURE:
<223> OTHER INFORMATION: Synthetic polynucleotide

```
<400> SEQUENCE: 7
agcacccaca tagtcaagat                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 8
cgtatcactg gactgattgg                                              20

<210> SEQ ID NO 9
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 9

Ala Lys Pro Arg Pro Pro Arg Pro Leu Pro Val Ala Cys
1               5                   10

<210> SEQ ID NO 10
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 10
cagtccagtg atacg                                                   15
```

LIGHT HARVESTING MULTICHROMOPHORE COMPOSITIONS AND METHODS OF USING THE SAME

CROSS-REFERENCING

This patent application is a continuation-in-part of: U.S. application Ser. No. 13/356,500, filed on Jan. 23, 2012 which is a continuation of U.S. application Ser. No. 11/746,055, filed May 8, 2007, which is a continuation of U.S. application Ser. No. 10/600,286, filed Jun. 20, 2003, which claims the benefit of U.S. Provisional Application No. 60/406,266, filed Aug. 26, 2002 and U.S. Provisional Application No. 60/390,524, filed on Jun. 20, 2002, which applications are incorporated herein by reference for all purposes; and this patent application is related to and claims the benefit of U.S. application Ser. No. 14/460,245, filed on Aug. 14, 2014, which is a continuation of U.S. application Ser. No. 14/086,532, filed Nov. 21, 2013, which is a continuation of U.S. application Ser. No. 13/544,303, filed Jul. 9, 2012, which is a continuation of U.S. application Ser. No. 12/632,734, filed Dec. 7, 2009, which is a continuation of U.S. application Ser. No. 11/854,365, filed Sep. 12, 2007, which is a divisional of U.S. application Ser. No. 10/648,945, filed Aug. 26, 2003, which claims the benefit of U.S. Provisional Application No. 60/406,266, filed Aug. 26, 2002; U.S. application Ser. No. 10/779,412, filed on Feb. 13, 2004, which claims the benefit of U.S. Provisional Application No. 60/447,860, filed Feb. 13, 2003; and U.S. application Ser. No. 13/075,172, filed on Mar. 29, 2011 which is a continuation of U.S. application Ser. No. 11/561,893, filed Nov. 21, 2006, which is a divisional of U.S. application Ser. No. 10/666,333, filed Sep. 17, 2003; which applications are incorporated herein by reference for all purposes.

GOVERNMENT SUPPORT

The following invention was made with support from grant number DMR-0097611, awarded by the National Science Foundation. The government has certain rights in the invention.

INTRODUCTION

Dyes which, when irradiated with light of a wavelength absorbed by these substances, emit light of a (usually) different wavelength are referred to as fluorescent dyes. Fluorescent dyes find us in a variety of applications in biochemistry, biology and medicine, e.g. in diagnostic kits, in microscopy or in drug screening. Fluorescent dyes are characterized by a number of parameters allowing a user to select a suitable dye depending on the desired purpose. This includes the excitation wavelength maximum, the emission wavelength maximum, the Stokes shift, the extinction coefficient .epsilon., the fluorescence quantum yield, and the fluorescence lifetime. Dyes may be selected according to the application of interest to, e.g., allow penetration of exciting radiation into biological, to minimize background fluorescence and to achieve a high signal-to-noise ratio.

Molecular recognition involves the specific binding of two molecules. Molecules which have binding specificity for a target biomolecule find use in a variety of research and diagnostic applications, such as the labelling and separation of analytes, flow cytometry, in situ hybridization, enzyme-linked immunosorbent assays (ELISAs), western blot analysis, magnetic cell separations and chromatography. Target biomolecules may be detected by labelling with a dye.

SUMMARY

Light harvesting luminescent multichromophores that are configured upon excitation to transfer energy to, and amplify the emission from, an acceptor signaling chromophore in energy-receiving proximity therewith are provided. Also provided are compositions for labelling a target. The labelling composition may include a donor light harvesting multichromophore and an acceptor signaling chromophore in energy-receiving proximity to the donor light harvesting multichromophore. Also provided is an aqueous composition for labelling a target, including: a donor light harvesting multichromophore; an acceptor signaling chromophore in energy-receiving proximity therewith; and a sensor biomolecule. Methods for using the subject compositions to detect a target are also provided.

BRIEF DESCRIPTION OF THE FIGURES

It is understood that the drawings, described below, are for illustration purposes only. The drawings are not intended to limit the scope of the present teachings in any way.

DEFINITIONS

Figure 1:
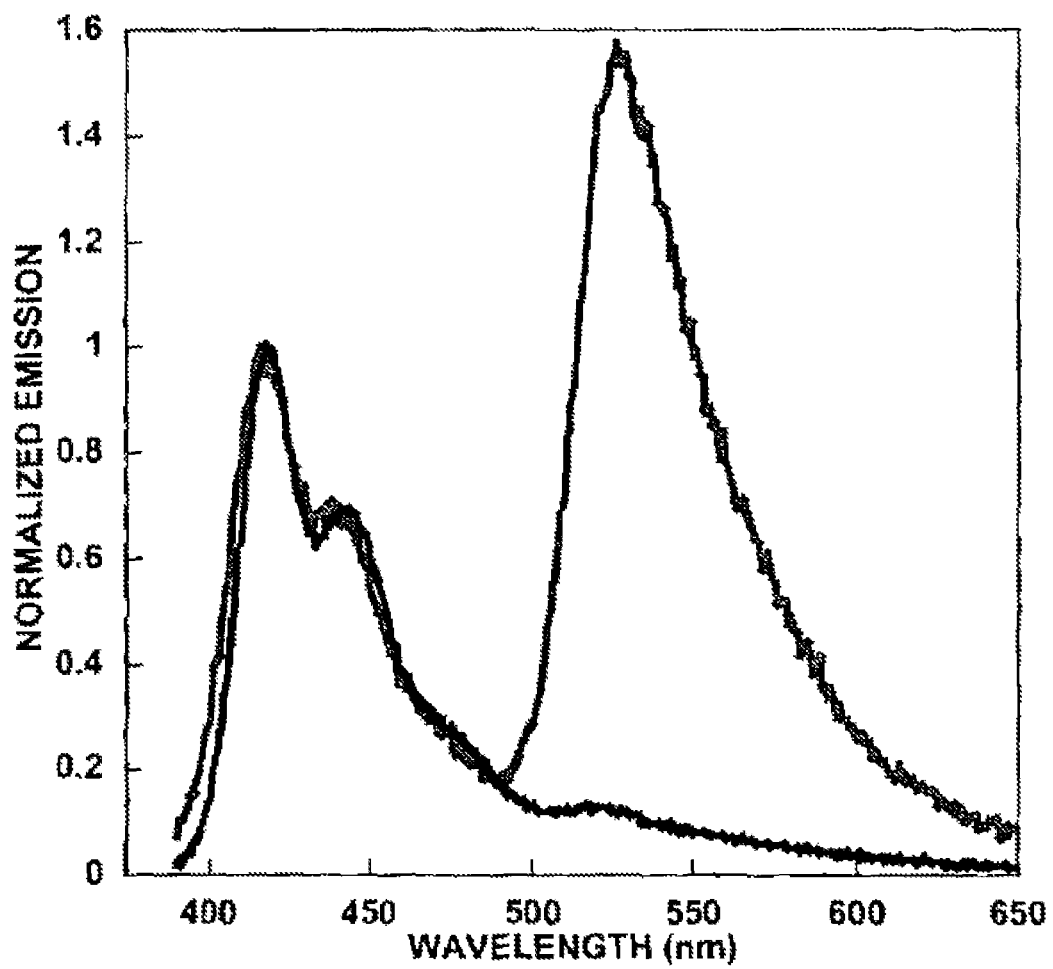
FIG. 1 presents the emission spectra of a composition including a signaling chromophore (e.g. PNA-C*) that is either connected to conjugated polymer 1 (e.g., via binding of complementary DNA to PNA-C*) or not connected to polymer 1 (e.g., when non-complementary DNA fails to bind to PNA-C*), by excitation of polymer 1. PNA-C* and the respective DNA were added together in water at pH=5.5. The spectra are normalized with respect to the emission of polymer 1.

Before the present invention is described in further detail, it is to be understood that this invention is not limited to the particular methodology, devices, solutions or apparatuses described, as such methods, devices, solutions or apparatuses can, of course, vary. It is also to be understood that the terminology used herein is for the purpose of describing particular embodiments only, and is not intended to limit the scope of the present invention.

Use of the singular forms "a," "an," and "the" include plural references unless the context clearly dictates otherwise. Thus, for example, reference to "a target polynucleotide" includes a plurality of target polynucleotides, reference to "a signaling chromophore" includes a plurality of such chromophores, reference to "a sensor PNA" includes a plurality of sensor PNAs, and the like. Additionally, use of specific plural references, such as "two," "three," etc., read on larger numbers of the same subject unless the context clearly dictates otherwise.

Terms such as "connected," "attached," "linked" and conjugated are used interchangeably herein and encompass direct as well as indirect connection, attachment, linkage or conjugation unless the context clearly dictates otherwise.

Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention. Where a value being discussed has inherent limits, for example where a component can be present at a concentration of from 0 to 100%, or where the pH of an aqueous solution can range from 1 to 14, those inherent limits are specifically disclosed. Where a value is explicitly recited, it is to be understood that values which are about the same quantity or amount as the recited value are also within the scope of the invention, as are ranges based thereon. Where a combination is disclosed, each subcombination of the elements of that combination is also specifically disclosed and is within the scope of the invention.

Conversely, where different elements or groups of elements are disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

Unless defined otherwise or the context clearly dictates otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

All publications mentioned herein are hereby incorporated by reference for the purpose of disclosing and describing the particular materials and methodologies for which the reference was cited. The publications discussed herein are provided solely for their disclosure prior to the filing date of the present application. Nothing herein is to be construed as an admission that the invention is not entitled to antedate such disclosure by virtue of prior invention.

In describing the present invention, the following terms will be employed, and are intended to be defined as indicated below.

The terms "polynucleotide," "oligonucleotide," "nucleic acid" and "nucleic acid molecule" are used interchangeably herein to refer to a polymeric form of nucleotides of any length, and may comprise ribonucleotides, deoxyribonucleotides, analogs thereof, or mixtures thereof. These terms refer only to the primary structure of the molecule. Thus, the terms include triple-, double- and single-stranded deoxyribonucleic acid ("DNA"), as well as triple-, double- and single-stranded ribonucleic acid ("RNA"). It also includes modified, for example by alkylation and/or by capping, and unmodified forms of the polynucleotide. "Complementary" or "substantially complementary" refers to the ability of a first specific binding member to specifically bind to a second specific binding member (e.g., hybridize or base pair between nucleotides or nucleic acids, such as, for instance, between a sensor peptide nucleic acid and a target polynucleotide). Complementary nucleotides are, generally, A and T (or A and U), or C and G. Two single-stranded polynucleotides or PNAs are said to be substantially complementary when the bases of one strand, optimally aligned and compared and with appropriate insertions or deletions, pair with at least about 80% of the bases of the other strand, usually at least about 90% to 95% and more preferably from about 98 to 100%.

Alternatively, substantial complementarity exists when a polynucleotide or PNA will hybridize under selective hybridization conditions to its complement. Typically, selective hybridization will occur when there is at least about 65% complementary over a stretch of at least 14 to 25 bases, preferably at least about 75%, more preferably at least about 90% complementary. See, M. Kanehisa Nucleic Acids Res. 12:203 (1984).

"Preferential binding" or "preferential hybridization" refers to the increased propensity of one specific binding member (e.g., a polynucleotide or PNA) to bind to its complementary specific binding member in a sample as compared to another noncomplementary component in the sample.

"Polypeptide" and "protein" are used interchangeably herein and include a molecular chain of amino acids linked through peptide bonds. The terms do not refer to a specific length of the product. Thus, "peptides," "oligopeptides," and "proteins" are included within the definition of polypeptide. The terms include polypeptides containing modifications of the polypeptide, for example, glycosylations, acetylations, phosphorylations, and sulphations. In addition, protein fragments, analogs (including amino acids not encoded by the genetic code, e.g. homocysteine, ornithine, D-amino acids, and creatine), natural or artificial mutants or variants or combinations thereof, fusion proteins, and proteins comprising derivatized residues (e.g. alkylation of amine groups, acetylations or others esterifications of carboxyl groups) and the like are included within the meaning of polypeptide.

"Multiplexing" herein refers to an assay or other analytical method in which multiple analytes can be assayed simultaneously.

"Optional" or "optionally" means that the subsequently described event or circumstance may or may not occur, and that the description includes instances where the event or circumstance occurs singly or multiply and instances in which it does not occur at all. For example, the phrase "optionally substituted alkyl" means an alkyl moiety that may or may not be substituted and the description includes both unsubstituted, monosubstituted, and polysubstituted alkyls.

"Alkyl" refers to a branched, unbranched or cyclic saturated hydrocarbon group of 1 to 24 carbon atoms optionally substituted at one or more positions, and includes polycyclic compounds. Examples of alkyl groups include optionally substituted methyl, ethyl, n-propyl, isopropyl, n-butyl, s-butyl, t-butyl, n-pentyl, isopentyl, neopentyl, n-hexyl, n-heptyl, n-octyl, n-decyl, hexyloctyl, tetradecyl, hexadecyl, eicosyl, tetracosyl and the like, as well as cycloalkyl groups such as cyclopropyl, cyclobutyl, cyclopentyl, cyclohexyl, cycloheptyl, cyclooctyl, adamantyl, and norbornyl. The term "lower alkyl" refers to an alkyl group of 1 to 6 carbon atoms, preferably 1 to 4 carbon atoms. Exemplary substituents on substituted alkyl groups include hydroxyl, cyano, alkoxy, $=O$, $=S$, $-NO_2$, halogen, haloalkyl, heteroalkyl, carboxyalkyl, amine, amide, thioether and $-SH$.

"Alkoxy" refers to an "—Oalkyl" group, where alkyl is as defined above. A "lower alkoxy" group intends an alkoxy group containing one to six, more preferably one to four, carbon atoms.

"Alkenyl" refers to a branched, unbranched or cyclic hydrocarbon group of 2 to 24 carbon atoms containing at least one carbon-carbon double bond optionally substituted at one or more positions. Examples of alkenyl groups include ethenyl, 1-propenyl, 2-propenyl (allyl), 1-methylvinyl, cyclopropenyl, 1-butenyl, 2-butenyl, isobutenyl, 1,4-butadienyl, cyclobutenyl, 1-methylbut-2-enyl, 2-methylbut-2-en-4-yl, prenyl, pent-1-enyl, pent-3-enyl, 1,1-dimethylallyl, cyclopentenyl, hex-2-enyl, 1-methyl-1-ethylallyl, cyclohexenyl, heptenyl, cycloheptenyl, octenyl, cyclooctenyl, decenyl, tetradecenyl, hexadecenyl, eicosenyl, tetracosenyl and the like. Preferred alkenyl groups herein contain 2 to 12 carbon atoms. The term "lower alkenyl" intends an alkenyl group of 2 to 6 carbon atoms, preferably 2 to 4 carbon atoms. The term "cycloalkenyl" intends a cyclic alkenyl group of 3 to 8, preferably 5 or 6, carbon atoms. Exemplary substituents on substituted alkenyl groups include hydroxyl, cyano, alkoxy, =O, =S, —NO$_2$, halogen, haloalkyl, heteroalkyl, amine, thioether and —SH.

"Alkenyloxy" refers to an "—Oalkenyl" group, wherein alkenyl is as defined above.

"Alkylaryl" refers to an alkyl group that is covalently joined to an aryl group. Preferably, the alkyl is a lower alkyl. Exemplary alkylaryl groups include benzyl, phenethyl, phenopropyl, 1-benzylethyl, phenobutyl, 2-benzylpropyl and the like.

"Alkylaryloxy" refers to an "—Oalkylaryl" group, where alkylaryl is as defined above.

"Alkynyl" refers to a branched or unbranched hydrocarbon group of 2 to 24 carbon atoms containing at least one —C≡C— triple bond, optionally substituted at one or more positions. Examples of alkynyl groups include ethynyl, n-propynyl, isopropynyl, propargyl, but-2-ynyl, 3-methylbut-1-ynyl, octynyl, decynyl and the like. Preferred alkynyl groups herein contain 2 to 12 carbon atoms. The term "lower alkynyl" intends an alkynyl group of 2 to 6, preferably 2 to 4, carbon atoms, and one —C≡C— triple bond. Exemplary substituents on substituted alkynyl groups include hydroxyl, cyano, alkoxy, =O, =S, —NO2, halogen, haloalkyl, heteroalkyl, amine, thioether and —SH.

"Amide" refers to —C(O)NR'R", where R' and R" are independently selected from hydrogen, alkyl, aryl, and alkylaryl.

"Amine" refers to an —N(R')R" group, where R' and R" are independently selected from hydrogen, alkyl, aryl, and alkylaryl.

"Aryl" refers to an aromatic group that has at least one ring having a conjugated pi electron system and includes carbocyclic, heterocyclic, bridged and/or polycyclic aryl groups, and can be optionally substituted at one or more positions. Typical aryl groups contain 1 to 5 aromatic rings, which may be fused and/or linked. Exemplary aryl groups include phenyl, furanyl, azolyl, thiofuranyl, pyridyl, pyrimidyl, pyrazinyl, triazinyl, biphenyl, indenyl, benzofuranyl, indolyl, naphthyl, quinolinyl, isoquinolinyl, quinazolinyl, pyridopyridinyl, pyrrolopyridinyl, purinyl, tetralinyl and the like. Exemplary substituents on optionally substituted aryl groups include alkyl, alkoxy, alkylcarboxy, alkenyl, alkenyloxy, alkenylcarboxy, aryl, aryloxy, alkylaryl, alkylaryloxy, fused saturated or unsaturated optionally substituted rings, halogen, haloalkyl, heteroalkyl, —S(O)R, sulfonyl, —SO$_3$R, —SR, —NO$_2$, —NRR', —OH, —CN, —C(O)R, —OC(O)R, —NHC(O)R, —(CH$_2$)$_n$CO$_2$R or —(CH$_2$)$_n$CONRR' where n is 0-4, and wherein R and R' are independently H, alkyl, aryl or alkylaryl.

"Aryloxy" refers to an "—Oaryl" group, where aryl is as defined above.

"Carbocyclic" refers to an optionally substituted compound containing at least one ring and wherein all ring atoms are carbon, and can be saturated or unsaturated.

"Carbocyclic aryl" refers to an optionally substituted aryl group wherein the ring atoms are carbon.

"Halo" or "halogen" refers to fluoro, chloro, bromo or iodo. "Halide" refers to the anionic form of the halogens.

"Haloalkyl" refers to an alkyl group substituted at one or more positions with a halogen, and includes alkyl groups substituted with only one type of halogen atom as well as alkyl groups substituted with a mixture of different types of halogen atoms. Exemplary haloalkyl groups include trihalomethyl groups, for example trifluoromethyl.

"Heteroalkyl" refers to an alkyl group wherein one or more carbon atoms and associated hydrogen atom(s) are replaced by an optionally substituted heteroatom, and includes alkyl groups substituted with only one type of heteroatom as well as alkyl groups substituted with a mixture of different types of heteroatoms. Heteroatoms include oxygen, sulfur, and nitrogen. As used herein, nitrogen heteroatoms and sulfur heteroatoms include any oxidized form of nitrogen and sulfur, and any form of nitrogen having four covalent bonds including protonated forms. An optionally substituted heteroatom refers to replacement of one or more hydrogens attached to a nitrogen atom with alkyl, aryl, alkylaryl or hydroxyl.

"Heterocyclic" refers to a compound containing at least one saturated or unsaturated ring having at least one heteroatom and optionally substituted at one or more positions. Typical heterocyclic groups contain 1 to 5 rings, which may be fused and/or linked, where the rings each contain five or six atoms. Examples of heterocyclic groups include piperidinyl, morpholinyl and pyrrolidinyl. Exemplary substituents for optionally substituted heterocyclic groups are as for alkyl and aryl at ring carbons and as for heteroalkyl at heteroatoms.

"Heterocyclic aryl" refers to an aryl group having at least 1 heteroatom in at least one aromatic ring. Exemplary heterocyclic aryl groups include furanyl, thienyl, pyridyl, pyridazinyl, pyrrolyl, N-lower alkyl-pyrrolo, pyrimidyl, pyrazinyl, triazinyl, tetrazinyl, triazolyl, tetrazolyl, imidazolyl, bipyridyl, tripyridyl, tetrapyridyl, phenazinyl, phenanthrolinyl, purinyl and the like.

"Hydrocarbyl" refers to hydrocarbyl substituents containing 1 to about 20 carbon atoms, including branched, unbranched and cyclic species as well as saturated and unsaturated species, for example alkyl groups, alkylidenyl groups, alkenyl groups, alkylaryl groups, aryl groups, and the like. The term "lower hydrocarbyl" intends a hydrocarbyl group of one to six carbon atoms, preferably one to four carbon atoms.

A "substituent" refers to a group that replaces one or more hydrogens attached to a carbon or nitrogen. Exemplary substituents include alkyl, alkylidenyl, alkylcarboxy, alkoxy, alkenyl, alkenylcarboxy, alkenyloxy, aryl, aryloxy, alkylaryl, alkylaryloxy, —OH, amide, carboxamide, carboxy, sulfonyl, =O, =S, —NO$_2$, halogen, haloalkyl, fused saturated or unsaturated optionally substituted rings, —S(O)R, —SO$_3$R, —SR, —NRR', —OH, —CN, —C(O)R, —OC(O) R, —NHC(O)R, —(CH$_2$)$_n$CO$_2$R or —(CH$_2$)$_n$CONRR' where n is 0-4, and wherein R and R' are independently H, alkyl, aryl or alkylaryl. Substituents also include replacement of a carbon atom and one or more associated hydrogen atoms with an optionally substituted heteroatom.

"Sulfonyl" refers to —S(O)$_2$R, where R is alkyl, aryl, —C(CN)=C-aryl, —CH2CN, alkylaryl, or amine.

"Thioamide" refers to —C(S)NR'R", where R' and R" are independently selected from hydrogen, alkyl, aryl, and alkylaryl.

"Thioether" refers to —SR, where R is alkyl, aryl, or alkylaryl.

The term "antibody" as used herein includes antibodies obtained from both polyclonal and monoclonal preparations, as well as: hybrid (chimeric) antibody molecules (see, for example, Winter et al. (1991) Nature 349:293-299; and U.S. Pat. No. 4,816,567); F(ab')2 and F(ab) fragments; Fv molecules (noncovalent heterodimers, see, for example, Inbar et al. (1972) Proc Natl Acad Sci USA 69:2659-2662; and Ehrlich et al. (1980) Biochem 19:4091-4096); single-chain Fv molecules (sFv) (see, for example, Huston et al. (1988) Proc Natl Acad Sci USA 85:5879-5883); dimeric and trimeric antibody fragment constructs; minibodies (see, e.g., Pack et al. (1992) Biochem 31:1579-1584; Cumber et al. (1992) J Immunology 1496:120-126); humanized antibody molecules (see, for example, Riechmann et al. (1988) Nature 332:323-327; Verhoeyan et al. (1988) Science 239:1534-1536; and U.K. Patent Publication No. GB 2,276,169, published 21 Sep. 1994); and, any functional fragments obtained from such molecules, wherein such fragments retain specific-binding properties of the parent antibody molecule.

As used herein, the term "monoclonal antibody" refers to an antibody composition having a homogeneous antibody population. The term is not limited regarding the species or source of the antibody, nor is it intended to be limited by the manner in which it is made. Thus, the term encompasses antibodies obtained from murine hybridomas, as well as human monoclonal antibodies obtained using human hybridomas or from murine hybridomas made from mice expression human immunoglobulin chain genes or portions thereof. See, e.g., Cote, et al. Monoclonal Antibodies and Cancer Therapy, Alan R. Liss, 1985, p. 77.

DETAILED DESCRIPTION

As summarized above, compositions including luminescent light harvesting multichromophores that are configured upon excitation to transfer energy to, and amplify the emission from, an acceptor signaling chromophore in energy-receiving proximity therewith are provided. The light harvesting multichromophores find use in a variety of applications, including analyte detection applications.

Light Harvesting, Luminescent Multichromophore Systems

Luminescent light harvesting multichromophore systems are efficient light absorbers by virtue of the multiple chromophores they include. Light harvesting multichromophores of interest include, but are not limited to, conjugated polymers, aggregates of conjugated molecules, luminescent dyes attached via side chains to saturated polymers, semiconductor quantum dots and dendritic structures. In some instances, the light harvesting multichromophore system includes a light harvesting conjugated polymer. For example, each repeat unit on a conjugated polymer can be considered as a contributing chromophore, quantum dots are made up of many atoms, a saturated polymer can be functionalized with many luminescent dye molecules on side chains, and dendrimers can be synthesized containing many covalently bonded individual chromophores. Attachment of chromophore assemblies onto solid supports, such as polymer beads or surfaces, can also be used for light harvesting.

In some instances, the water soluble, light harvesting multichromophore has a luminescent emission spectrum, i.e., the multichromophore is itself luminescent. In some cases, water soluble, light harvesting multichromophore has high luminescence quantum efficiency. In certain cases, the water soluble, light harvesting multichromophore has high fluorescent efficiency. Light harvesting multichromophore systems can also efficiently transfer energy to nearby luminescent species (e.g., "signaling chromophores"). Mechanisms for energy transfer include, for example, resonant energy transfer (Förster (or fluorescence) resonance energy transfer, FRET), quantum charge exchange (Dexter energy transfer) and the like. In some cases, however, these energy transfer mechanisms are relatively short range; that is, close proximity of the light harvesting multichromophore system to the signaling chromophore is required for efficient energy transfer. As used herein, the term "energy receiving proximity" refers to an arrangement of the light harvesting multichromophore system and the signaling chromophore sufficient for efficient energy transfer, e.g., via FRET. Under conditions for efficient energy transfer, amplification of the emission from the signaling chromophore occurs when the number of individual chromophores in the light harvesting multichromophore system is large: that is, the emission from the signaling chromophore is more intense when the incident light (the "pump light") is at a wavelength which is absorbed by the light harvesting multichromophore system than when the signaling chromophore is directly excited by the pump light.

When the average distance between the light harvesting multichromophore and the signaling chromophore is too large for effective energy transfer, there is little or no emission from the signaling chromophore. As such, the light harvesting multichromophore may be configured upon excitation to transfer energy to, and amplify the emission from, an acceptor signaling chromophore in energy-receiving proximity therewith.

The light harvesting multichromophore and the signaling chromophore (C*) are selected so that the absorption bands of the two chromophores have minimal overlap and so that the luminescent emission spectra of the two species are at different wavelengths. In some instances, the water soluble, light harvesting multichromophore has a luminescent emission spectrum, i.e., the multichromophore is luminescent.

As shown by Förster, dipole-dipole interactions lead to long-range resonance energy transfer (FRET) from a donor chromophore to an acceptor chromophore. The energy transfer efficiency (E) is proportional to $1/r^6$, where r is the donor-acceptor distance, and the overlap integral, as shown in Equation 1.

$$E \propto \frac{1}{r^6} \int_0^\infty F_D(\lambda)\varepsilon_A(\lambda)\lambda^4 d\lambda \qquad (1)$$

The distance requirement for energy transfer in the compositions described herein may be controlled by the configuration of the donor and the acceptor. The overlap integral expresses the spectral overlap between the emission of the donor and the absorption of the acceptor. The components of the labelling composition and their relative configuration can be selected so that their optical properties meet this requirement.

In some instances, the light harvesting multichromophores described herein are soluble in aqueous solutions and other polar solvents, and in some cases are soluble in water, i.e., they are water-soluble. By "water-soluble" is meant that the material exhibits solubility in a predominantly aqueous solution, which, although comprising more than 50% by volume of water, does not exclude other substances from that solution, including without limitation buffers, blocking agents, co-solvents, salts, metal ions and detergents. It is understood that the light harvesting multichromophores may be selected and/or adapted to achieve a variety of desirable characteristics (such as water solubility) using any convenient methods and materials, such as the methods and materials described by N. Angelova and D. Hunkeler in "Rationalizing the design of polymeric biomaterials", TIBTECH, October 1999, 17, 409-421; and S. Zalipsky in "Functionalized poly(ethylene glycol) for preparation of biologically relevant conjugates", Bioconjugate Chemistry 1995, 6 (2), 150-165. In some instances, the light harvesting multichromophores include water-soluble groups which improve the water solubility of the molecules. In certain instances, the light harvesting multichromophore is conjugated to another water soluble molecule, such as a biomolecule. In certain cases, the light harvesting multichromophore is conjugated to a sensor.

Any convenient water-soluble groups (WSGs) may be utilized in the subject light harvesting multichromophores. The term "water-soluble group" refers to a functional group that is well solvated in aqueous environments and that imparts improved water solubility to the molecules to which it is attached. In some embodiments, a WSG increases the solubility of the multichromophore in a predominantly aqueous solution (e.g., as described herein), as compared to a multichromophore which lacks the WSG. The water soluble groups may be any convenient hydrophilic group that is well solvated in aqueous environments. In some cases, the hydrophilic water soluble group is charged, e.g., positively or negatively charged. In certain cases, the hydrophilic water soluble group is a neutral hydrophilic group. In some embodiments, the WSG is a hydrophilic polymer, e.g., a polyethylene glycol, a cellulose, a chitosan, or a derivative thereof.

As used herein, the terms "polyethylene oxide", "PEO", "polyethylene glycol" and "PEG" are used interchangeably and refer to a polymer including a chain described by the formula —($CH_2$—$CH_2$—O—)$_n$— or a derivative thereof. In some embodiments, "n" is 5000 or less, such as 1000 or less, 500 or less, 200 or less, 100 or less, 50 or less, 40 or less, 30 or less, 20 or less, 15 or less, such as 5 to 15, or 10 to 15. It is understood that the PEG polymer may be of any convenient length and may include a variety of terminal groups, including but not limited to, alkyl, aryl, hydroxyl, amino, acyl, acyloxy, and amido terminal groups.

Functionalized PEGs that may be adapted for use in the subject multichromophores include those PEGs described by S. Zalipsky in "Functionalized poly(ethylene glycol) for preparation of biologically relevant conjugates", Bioconjugate Chemistry 1995, 6 (2), 150-165.

Water soluble groups of interest include, but are not limited to, carboxylate, phosphonate, phosphate, sulfonate, sulfate, sulfinate, ester, polyethylene glycols (PEG) and modified PEGs, hydroxyl, amine, ammonium, guanidinium, polyamine and sulfonium, polyalcohols, straight chain or cyclic saccharides, primary, secondary, tertiary, or quaternary amines and polyamines, phosphonate groups, phosphinate groups, ascorbate groups, glycols, including, polyethers, —COOM', —$SO_3$M', —$PO_3$M', —$NR_3^+$, Y', ($CH_2CH_2O)_p$R and mixtures thereof, where Y' can be any halogen, sulfate, sulfonate, or oxygen containing anion, p can be 1 to 500, each R can be independently H or an alkyl (such as methyl) and M' can be a cationic counterion or hydrogen, —($CH_2CH_2O)_{yy}CH_2CH_2XR^{yy}$, —($CH_2CH_2O)_{yy}CH_2CH_2X$—, —$X(CH_2CH_2O)_{yy}CH_2CH_2$—, glycol, and polyethylene glycol, wherein yy is selected from 1 to 1000, X is selected from O, S, and $NR^{zz}$, and $R^{zz}$ and $R^{YY}$ are independently selected from H and C1-3 alkyl.

In some embodiments, the light harvesting multichromophore includes cationic WSGs and is polycationic. Any suitable cationic WSGs may be incorporated into the light harvesting multichromophores, including, but not limited to, ammonium groups, guanidinium groups, histidines, polyamines, pyridinium groups, and sulfonium groups.

The water solubility of light harvesting multichromophores (e.g., CPs), finds use in detecting biological targets, and in some cases is achieved by including water-soluble groups (e.g., hydrophilic groups, such as PEG or modified PEG groups or charged groups attached to the CP backbone). In some instances, the light harvesting multichromophores are conjugated polymers, which include sulfonate or carboxylate functionalities.

Exemplary multichromophores which can be used include, but are not limited to, conjugated polymers (which includes oligomers), saturated polymers or dendrimers incorporating multiple chromophores in any viable manner, and semiconductor nanocrystals (SCNCs). In some cases, the conjugated polymers, saturated polymers and dendrimers can be prepared to incorporate multiple WSGs or can be derivatized after synthesis. For example, in Example 4, Schemes 2 and 3 depict the preparation of conjugated polymers that may be adapted to include any convenient substituted alkyl (e.g., bromo-substituted alkyl) substituents. Any convenient substituents (such as water soluble groups) may be selected for inclusion in the subject conjugated polymers via polymer derivatization after polymer synthesis, e.g., via nucleophilic substitution of the bromoalkyl substitutent groups with any convenient nucleophilic groups to produce heteroalkyl substituted conjugated polymers.

In some embodiments, a water soluble light harvesting multichromophore is a conjugated polymer that includes water soluble groups. For example, water soluble conjugated molecules of interest which may be prepared according to the methods described herein include, but are not limited to, polymer 1 (where n=2-100,000), oligomer 1 and oligomer 2, shown below. In some instances, the water soluble light harvesting multichromophores have a structure selected from the formula of polymer 1, the formula of oligomer 1 or the formula of oligomer 2, depicted below. However, the specific molecular structures of polymer 1, oligomer 1 and oligomer 2, depicted below are not critical, and any water soluble light harvesting molecules can be used.

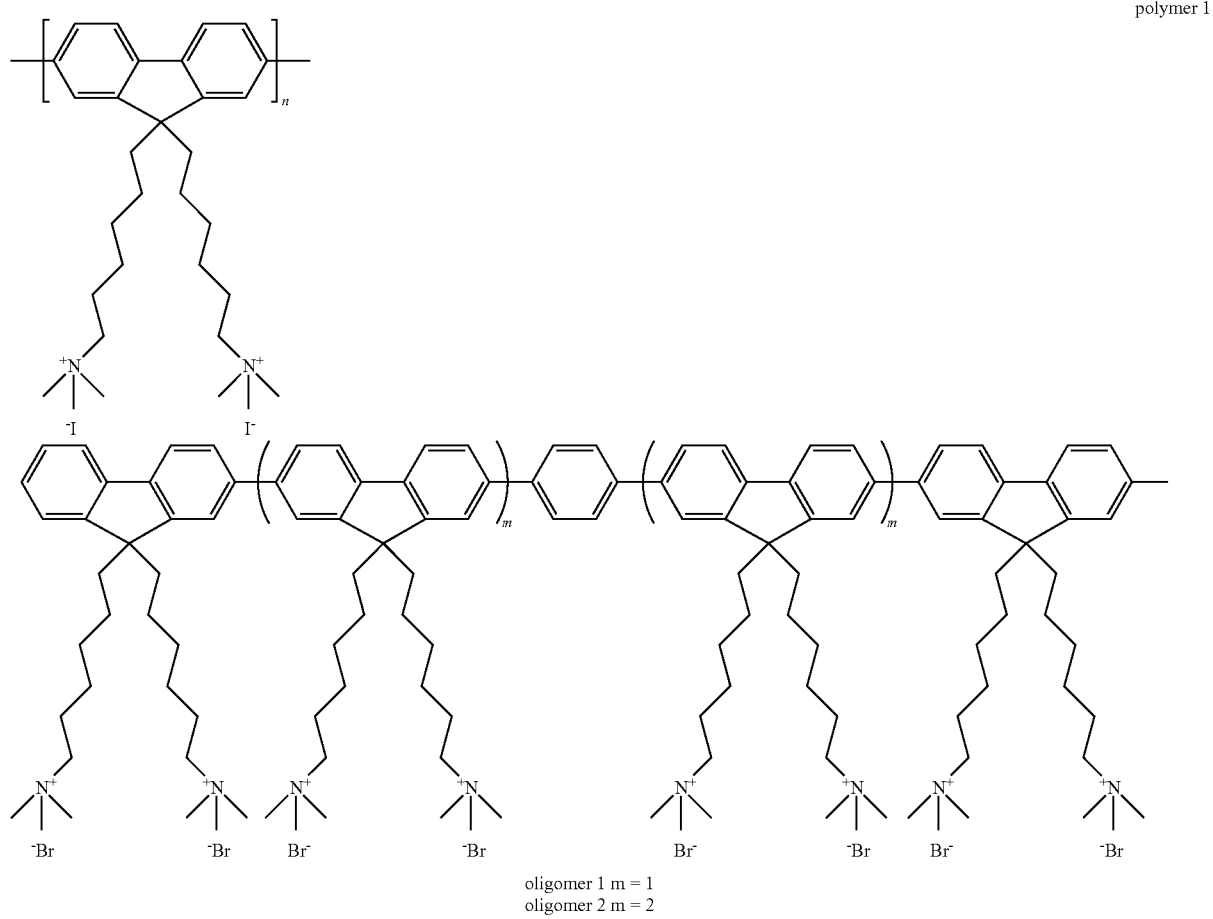

polymer 1 oligomer 1 m = 1
oligomer 2 m = 2

A specific example is shown in structure 1 where the water soluble conjugated polymer is poly((9,9-bis(6'-N,N,N-trimethylammonium)-hexyl)-fluorene phenylene) (denoted in the following as polymer 1). In some cases, the particular size of the subject conjugated polymers is not critical, so long as the CP is able to absorb light and transfer energy to signaling chromophores that are configured in energy receiving proximity. In some cases, values of "n" fall within the range of two to about 100,000. This specific molecular structure is not critical; any water soluble conjugated polymer with relatively high luminescence quantum efficiency can be used.

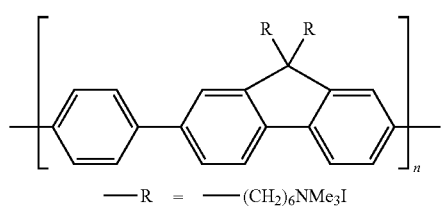

1

R = —(CH$_2$)$_6$NMe$_3$I

In some instances, the water soluble light harvesting multichromophore is a conjugated oligomer, such as a water soluble, cationic, luminescent conjugated oligomer, as shown below (denoted herein as oligomer 2):

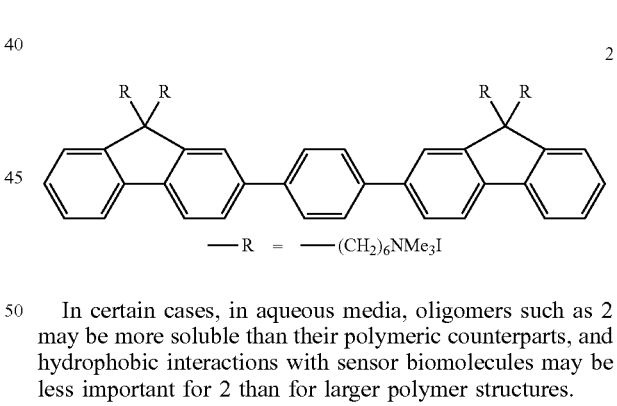

2

R = —(CH$_2$)$_6$NMe$_3$I

In certain cases, in aqueous media, oligomers such as 2 may be more soluble than their polymeric counterparts, and hydrophobic interactions with sensor biomolecules may be less important for 2 than for larger polymer structures.

Addition of organic solvents to the subject compositions, for example a water miscible organic solvent such as ethanol, can result in a decrease in background (C*) emission. The presence of the organic solvent can decrease hydrophobic interactions between the light harvesting multichromophore and another component of the assay and thereby reduce background signal.

Conjugated Polymers

In some embodiments, the light harvesting multichromophore is a conjugated polymer. Conjugated polymers (CPs) are characterized by a delocalized electronic structure and, in some cases, can be used as highly responsive optical reporters for chemical and biological targets. In a CP, the effective conjugation length may be substantially shorter than the length of the polymer chain, and thus the backbone may contain a large number of conjugated segments in close proximity. In some instances, conjugated polymers are efficient for light harvesting and provide for optical amplification via Förster energy transfer to a signalling chromophore. In certain instances, water-soluble CPs show exceptional fluorescence quenching efficiencies in the presence of acceptor in energy-receiving proximity and are of interest for transduction of biological recognition events, among other uses.

In one embodiment, a conjugated polymer is represented by Formula A:

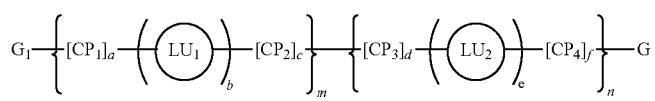

Formula A where:
CP$_1$, CP$_2$, CP$_3$, and CP$_4$ are optionally substituted conjugated polymer segments or oligomeric structures, and may be the same or different from one another;
LU$_1$ and LU$_2$ are each independently a linker unit;
G$_1$ and G are each independently a capping unit;
a, b, c, d, e and f are each independently 0 to 250; and
m and n are each independently 0 to 10,000, where m+n>1.

CP$_1$, CP$_2$, CP$_3$, and CP$_4$ may be independently aromatic repeat units, and, in some cases, may be selected from the group consisting of benzene, naphthalene, anthracene, fluorene, thiophene, furan, pyridine, and oxadiazole, each optionally substituted.

In some embodiments, the formula contains linker units LU$_1$ and LU$_2$ which may be angled linkers (e.g., as described herein) and, in some cases, can be mono- or polycyclic optionally substituted aryl groups having 5 to 20 atoms (e.g., an aromatic repeat unit of Table 1 or 2). The linker units may be evenly or randomly distributed along the polymer main chain. Aromatic rings of interest include those which also produce a spatial twist of the polymer main chain, preventing the conjugated polymer from forming a plane across that linker unit.

In some embodiments, LU$_1$ and LU$_2$ are independently selected from the group consisting of benzene derivatives incorporated into the polymer in the 1, 2 or 1,3-positions; naphthalene derivatives incorporated into the polymer in the 1,2-, 1,3-, 1,6-, 1,7-, 1,8-positions; anthracene derivatives incorporated into the polymer in the 1,2-, 1,3-, 1,6-, 1,7-, 1,8-, and 1,9-positions; biphenyl derivatives incorporated into the polymer in the 2,3-, 2,4-, 2,6-, 3,3'-, 3,4-, 3,5-, 2,2'-, 2,3'-, 2,4'-, and 3,4'-positions; and corresponding heterocycles. The position numbers are given with reference to unsubstituted carbon-based rings, but the same relative positions of incorporation in the polymer are encompassed in substituted rings and/or heterocycles should their distribution of substituents change the ring numbering.

In some instances, CP$_1$, CP$_2$, CP$_3$, CP$_4$, LU$_1$ and LU$_2$ are each optionally substituted at one or more positions with one or more groups selected from —R$^1$-A, —R$^2$-B, —R$^3$-C, —R$^4$-D and —R$^5$-I, which may be attached through bridging functional groups -E- and -F- (see e.g., the units depicted in Tables 1 and 2). In some instances, R$^1$, R$^2$, R$^3$, R$^4$ and R$^5$ are independently selected from alkyl, alkenyl, alkoxy, alkynyl, and aryl, alkylaryl, arylalkyl, and polyalkylene oxide, each optionally substituted, which may contain one or more heteroatoms, or may be not present. In some instances, R$^1$, R$^2$, R$^3$, R$^4$ and R$^5$ can be independently selected from C$_{1-22}$ alkyl, C$_{1-22}$ alkoxy, C$_{1-22}$ ester, polyalkylene oxide having from 1 to about 22 carbon atoms, cyclic crown ether having from 1 to about 22 carbon atoms, or not present. In some instances, R$^1$, R$^2$, R$^3$, R$^4$ and R$^5$ may be selected from straight or branched alkyl groups having 1 to about 12 carbon atoms, or alkoxy groups with 1 to about 12 carbon atoms. It is to be understood that more than one functional group may be appended to the rings as indicated in the formulas at one or more positions.

In some instances, A, B, C, D and I are independently selected from H, a WSG, —SiR'R"R'", —N$^+$R'R"R'", a guanidinium group, histidine, a polyamine, a pyridinium group, and a sulfonium group. In some instances, R', R" and R'" are independently selected from the group consisting of hydrogen, C$_{1-12}$ alkyl and C$_{1-12}$ alkoxy and C$_{3-10}$ cycloalkyl. In certain embodiments, R', R" and R'" are lower alkyl or lower alkoxy groups. In some embodiments, E and F are independently selected from not present, —O—, —S—, —C(O)—, —C(O)O—, —C(R)(R')—, —N(R')—, and —Si(R')(R"), wherein R' and R" are as defined above. In some embodiments, E and F are —O—. In some embodiments, E and F are not present. In some instances, A, B, C, D and I are H. In certain instances, A, B, C, D and I are independently a WSG.

In some cases, X is O, S, Se, —N(R')— or —C(R')(R")—, and Y and Z are independently selected from —C(R)= and —N=, where R, R' and R" are as defined above.

In certain instances, m and n are independently 0 to 10,000, wherein m+n>1. In some embodiments, m and n are each independently 0 to 20 and in some cases from 0 to 10. Each repeat of m and n may be the same as or different than the other repeats thereof. In some embodiments, b and e are independently 0 to 250, where b+e>1. In certain cases, a, c, d and f are independently 0 to 250. In some embodiments, b and e are each 0.

Any convenient capping units may be utilized in the conjugated polymers. In some instances, G and G$_1$ are capping units and may be the same or different. The capping units may be activated units that allow further chemical reaction to the terminal of the polymer chain. In some cases, G and G$_1$ may be a group that includes a reactive functional group suitable for conjugation to a biomolecule. Any convenient activated units may be utilized as capping units G and/or G$_1$ in the subject CPs. The capping units may be nonactivated termination units. In certain instances, G and G$_1$ can be independently selected from hydrogen, optionally substituted aryl, halogen substituted aryl, boronic acid substituted aryl, and boronate radical substituted aryl.

Also provided are conjugated polymer compositions of formula A where CP$_1$, CP$_2$, CP$_3$, CP$_4$, LU$_1$ and LU$_2$ are each optionally substituted at one or more positions with one or more groups selected from —R$^1$-A, —R$^2$-B, —R$^3$-C, —R$^4$-D and —R$^5$-I where A, B, C, D and I are each H, which may be attached via bridging functional groups -E- and -F-. In some instances, R$^1$, R$^2$, R$^3$, R$^4$ and R$^5$ are independently selected from alkyl, alkenyl, alkoxy, alkynyl, and aryl, alkylaryl, arylalkyl, and polyalkylene oxide, each optionally substituted, which may contain one or more heteroatoms, or may be not present. In some embodiments, E and F are independently selected from not present, —O—, —S—, —C(O)—, —C(O)O—, —C(R)(R')—, —N(R')—, and —Si(R')(R"), wherein R' and R" are as defined above.

In certain embodiments of Formula A, at least one of —R¹-A, —R²-B, —R³-C, —R⁴-D and —R⁵-I includes a water soluble group (WSG). In some instances, R³-C and —R⁴-D each independently include a water soluble group. In certain embodiments, —R¹-A, —R²-B and —R⁵-I are each H. In certain instances, E and R⁵-I are not present. In certain embodiments, R³ and R⁴ are alkyl, each optionally substituted.

In certain embodiments the light harvesting multichromophore is a conjugated polymer including a conjugated segment having the structure:

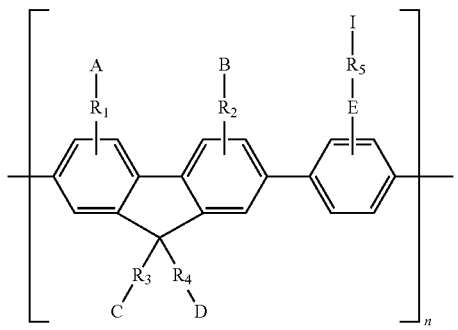

where n, E, —R¹-A, —R²-B, —R³-C, —R⁴-D and —R⁵-I are as defined above. In certain embodiments, at least one of —R¹-A, —R²-B, —R³-C, —R⁴-D and —R⁵-I includes a water soluble group (WSG). In some instances, R³-C and —R⁴-D each independently include a water soluble group. In certain embodiments, —R¹-A, —R²-B and —R⁵-I are each H. In certain instances, E and R⁵-I are not present. In certain embodiments, R³ and R⁴ are alkyl, each optionally substituted.

Aromatic repeat units of interest are shown in Table 1 below, and representative polymeric segments and oligomeric structures are shown in Table 2.

TABLE 1

Aromatic repeat units of interest for the construction of conjugated segments and oligomeric structures.

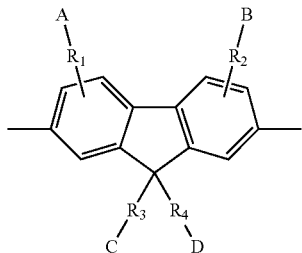

TABLE 1-continued

Aromatic repeat units of interest for the construction of conjugated segments and oligomeric structures.

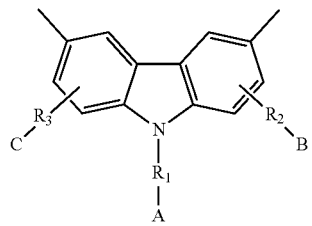

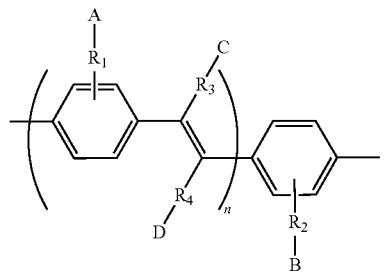

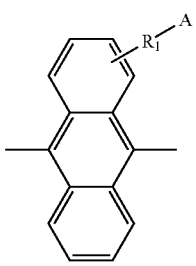

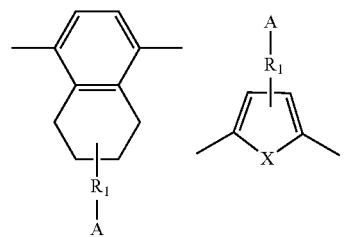

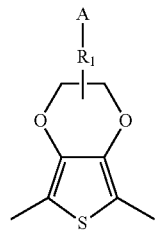

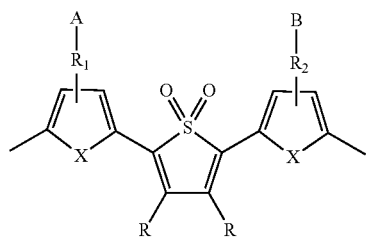

TABLE 1-continued
Aromatic repeat units of interest for the construction of conjugated segments and oligomeric structures.
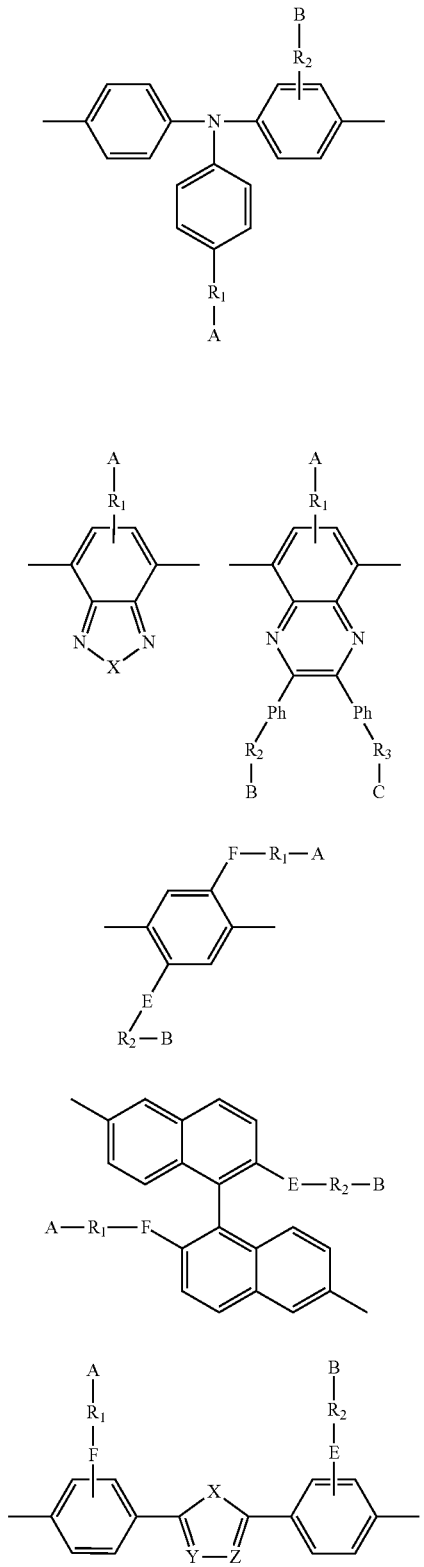
TABLE 2
Examples of conjugated segments and oligomeric structures of CPs
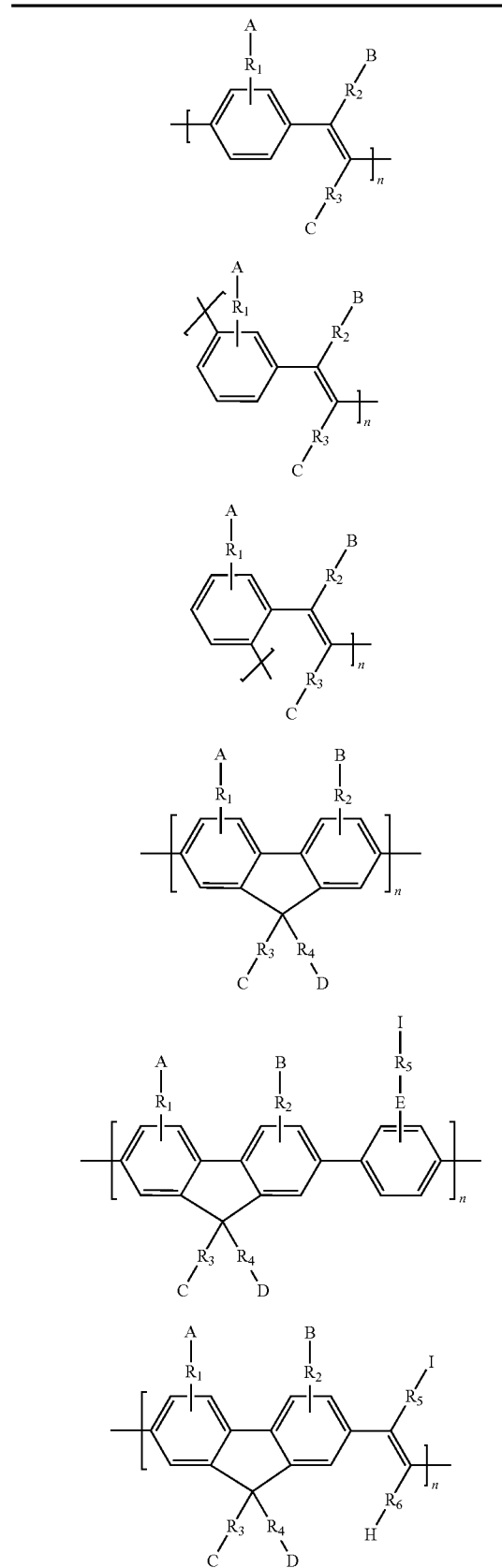

TABLE 2-continued
Examples of conjugated segments and oligomeric structures of CPs
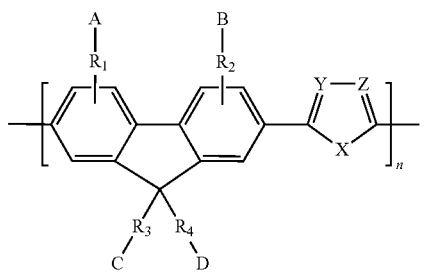
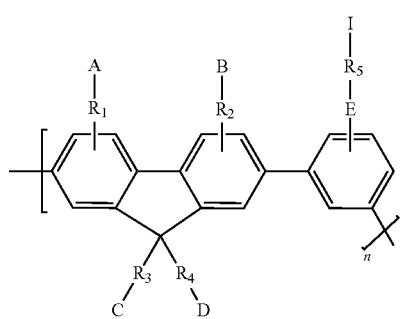
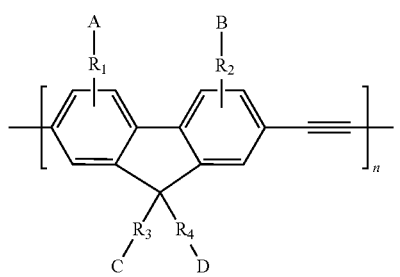
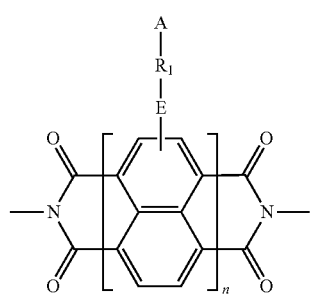
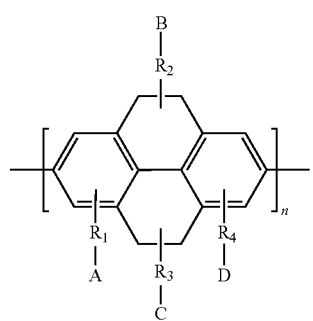
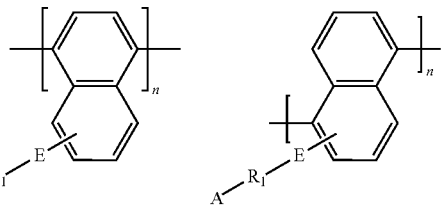
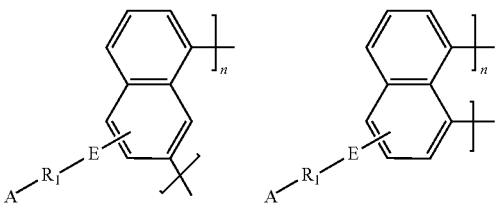
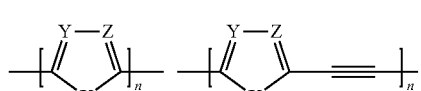
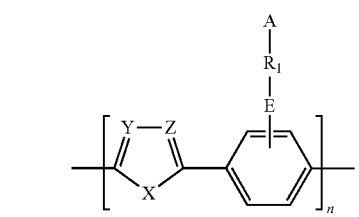
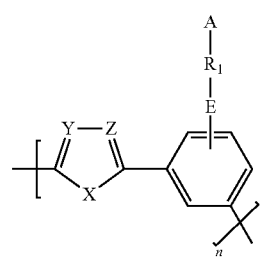
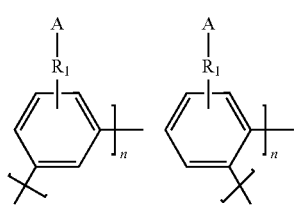
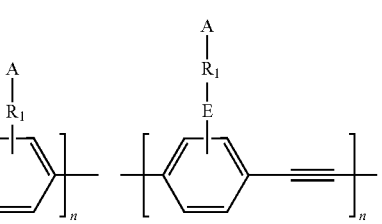
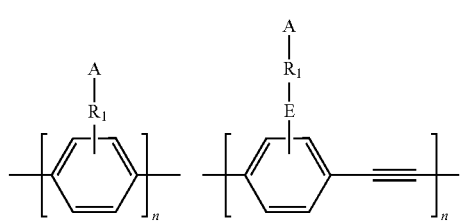

TABLE 2-continued
Examples of conjugated segments and oligomeric structures of CPs
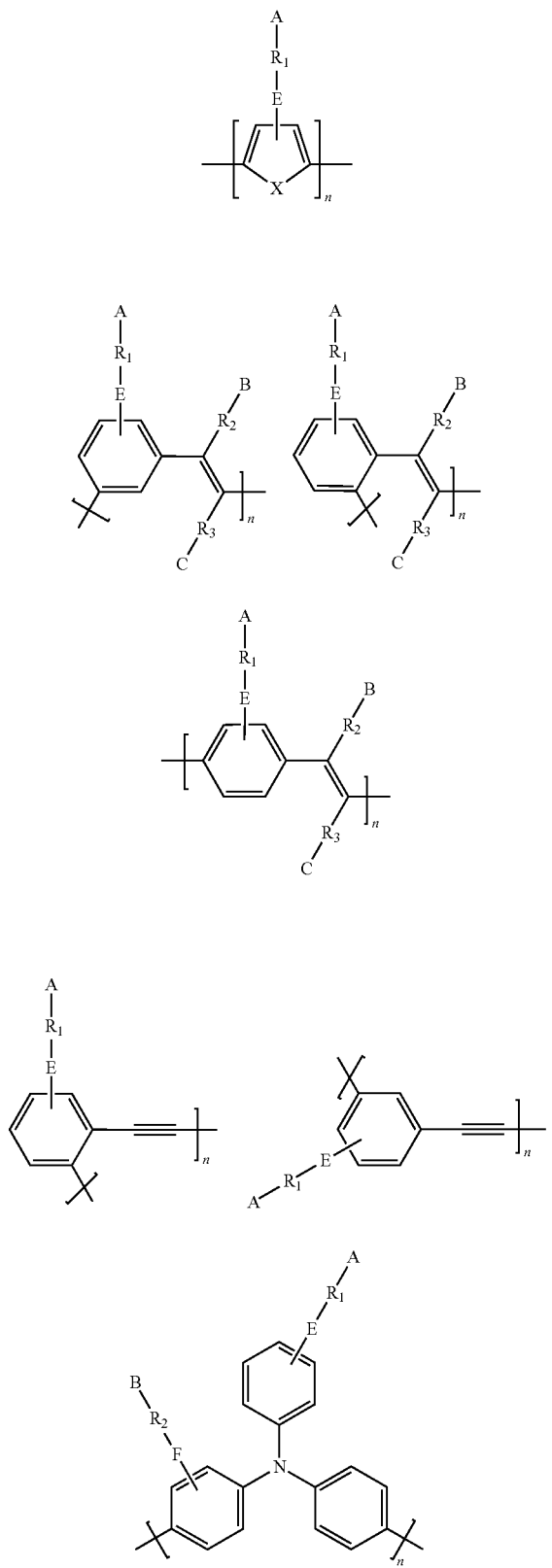
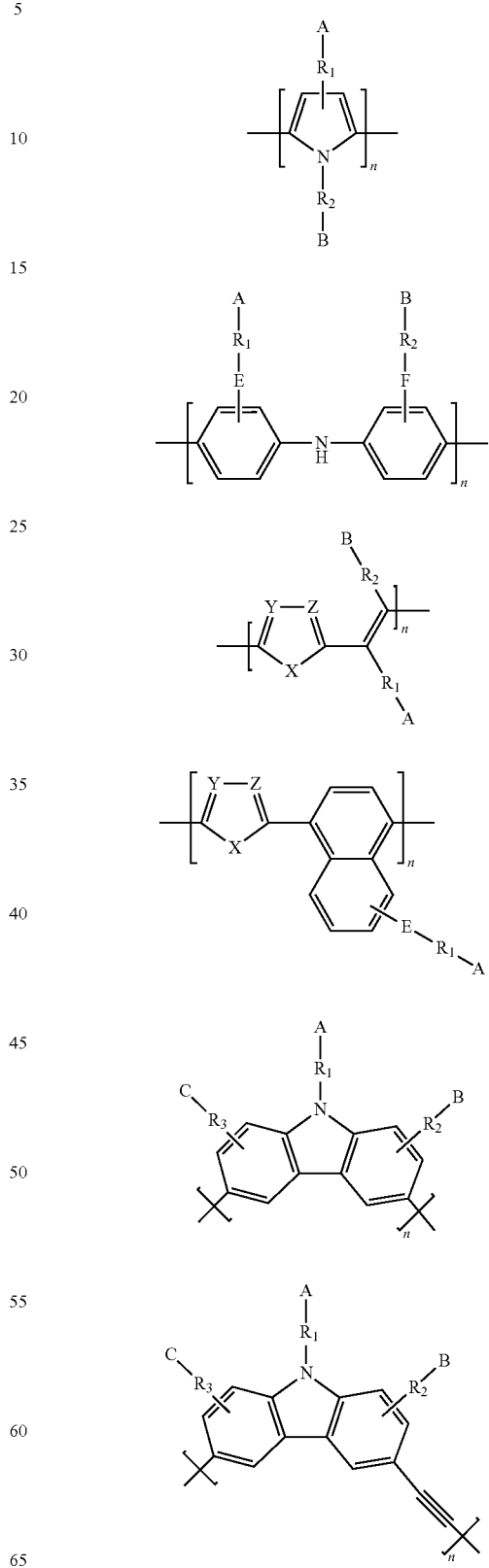

TABLE 2-continued

Examples of conjugated segments and oligomeric structures of CPs

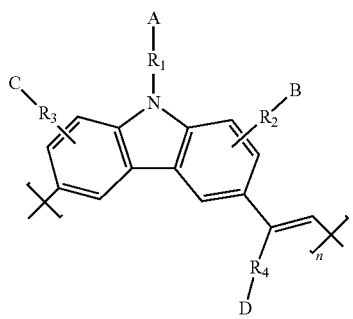

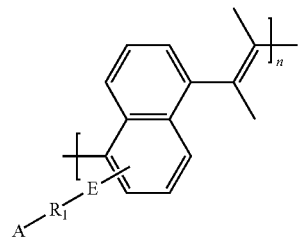

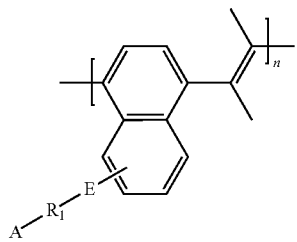

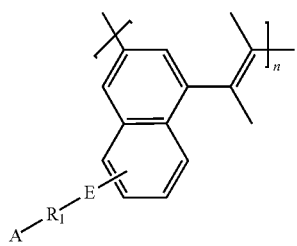

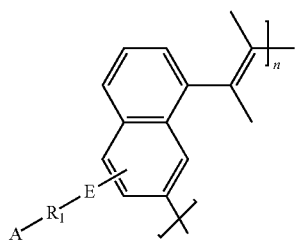

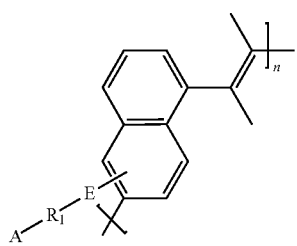

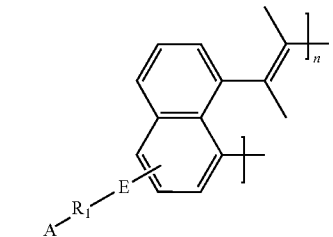

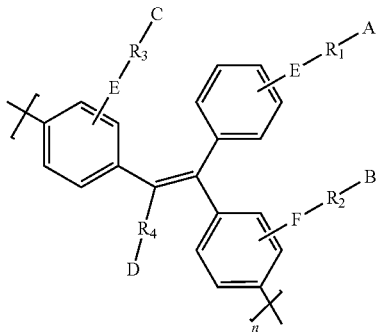

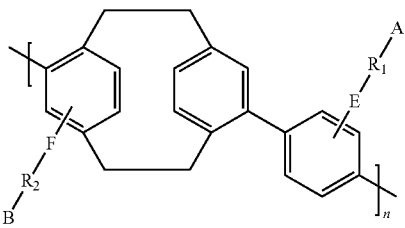

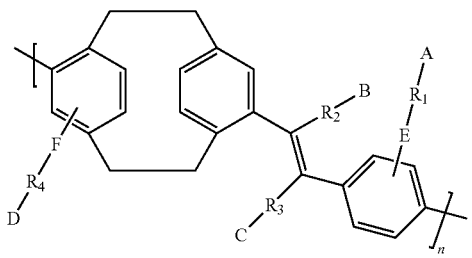

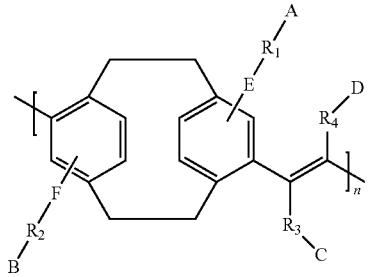

Conformationally Flexible CPs

Conjugated polymers (CPs) are efficient light-gathering molecules with properties desirable for a variety of applications. Conjugated polymers can serve as light harvesting materials and signal transducers in fluorescent biosensor applications. These molecules can detect, transduce and/or amplify chemical, biological or physical information into optical and/or electrical signals. CPs can provide the advantage of collective response relative to non-interacting small molecules. This collective response influences optoelectronic properties, such as Förster resonance energy transfer (FRET), electrical conductivity and fluorescence efficiency, properties which can be used to report, or "transduce," target analyte presence.

Conformationally Flexible CPs

Conjugated polymers (CPs) are efficient light-gathering molecules with properties desirable for a variety of applications. Conjugated polymers can serve as light harvesting materials and signal transducers in fluorescent biosensor applications. These molecules can detect, transduce and/or amplify chemical, biological or physical information into optical and/or electrical signals. CPs can provide the advantage of collective response relative to non-interacting small molecules. This collective response influences optoelectronic properties, such as Förster resonance energy transfer (FRET), electrical conductivity and fluorescence efficiency, properties which can be used to report, or "transduce," target analyte presence.

Aspects of the invention include conjugated polymers (CPs) including monomers which perturb the polymer's ability to form rigid-rod structures, allowing them to form a greater range of three-dimensional structures. The monomers may include aromatic molecules having attachment points to the adjacent subunits of the polymer which form an angle of greater than about 25°. The monomers may introduce a torsional twist in the conjugated polymer, thereby further disrupting the ability of the polymer to form a rigid-rod structure.

A synthetic method is also provided for producing CPs with a range of backbone regiochemistries. Such CPs exhibit facile energy transfer amongst polymer segments which results in similar emission properties and FRET function. In some instances, the flexible CPs are efficient excitation donors with respect to particular biomolecules and find use in bioassays that take advantage of the optical amplification of water-soluble conjugated polymers.

In one aspect, a plurality of CPs with different structures are provided, which may be in the form of a library. The CPs may be tested for any property of interest.

For example, the CPs may be tested for increased fluorescent efficiency, for decreased self-quenching, increased Stoke's shift, and for emission wavelength.

In some embodiments, modification of polymer shape is achieved through fractional incorporation of meta and para linkages on phenylene units adjacent to fluorenyl monomer units. The meta to para ratio may be controlled during the polymerization reaction by use of, for example, 1,3-phenylenebisboronic acid and 1,4-phenylenebisboronic acid in appropriate ratios. The corresponding polymers may have ratios of meta to para linkages ranging from 0 to 100%. In some cases, the introduction of the meta linkage not only permits shape control, but also provides the possibility of energy transfer along the polymer main chain, or between different polymer segments, since fragments containing a higher fraction of para linkages may be of lower energy level, and may behave as low energy traps.

Conformationally flexible conjugated polymers (CPs) may include angled linkers with a substitution pattern (or regiochemistry) capable of perturbing the polymers' ability to form rigid-rod structures, allowing the CPs to have a greater range of three-dimensional structures. The CPs may include at least three subunits with at least one angled linker, which may be internal and/or an end unit, and may comprise at least 4, 5, 6, 8, 10, 15, 20, 25 or more subunits. The CPs may include up to about 100, 200, 300, 500, 1000, 2000, 5000, 10000, 20000, 50000 or more subunits.

The angled linker(s) are optionally substituted aromatic molecules having at least two separate bonds to other polymer components (e.g., monomers, block polymers, end groups) that are capable of forming angles relative to one another which disrupt the overall ability of the polymer to form an extended rigid-rod structure (although significant regions exhibiting such structure may remain.) The angled linkers may be bivalent or polyvalent.

The angle which the angled linkers are capable of imparting to the polymeric structure is determined as follows. Where the two bonds to other polymeric components are coplanar, the angle can be determined by extending lines representing those bonds to the point at which they intersect, and then measuring the angle between them. Where the two bonds to other polymeric components are not coplanar, the angle can be determined as follows: a first line is drawn between the two ring atoms to which the bonds attach; two bond lines are drawn, one extending from each ring atom in the direction of its respective bond to the other polymeric component to which it is joined; the angle between each bond line and the first line is fixed; and the two ring atoms are then merged into a single point by shrinking the first line to a zero length; the angle then resulting between the two bond lines is the angle the angled linker imparts to the CP.

The angle which an angled linker is capable of imparting to the polymer is in some cases less than 155°, and may be less than 150°, less than 145°, less than 140°, less than 135°, less than 130°, less than 125°, less than 120°, less than 115°, less than 110°, less than 105°, less than 100°, less than 95°, less than 90°, less than 85°, less than 80°, less than 75°, less than 70°, less than 65°, less than 60°, less than 55°, or less than 50°. The angled linker may form an angle to its adjacent polymeric units of about 25°, 30°, 35°, 40°, 45°, 50°, 60° or more.

The angled linker may introduce a torsional twist in the conjugated polymer, thereby further disrupting the ability of the polymer to form a rigid-rod structure. For angled linkers having an internally rotatable bond, such as polysubstituted biphenyl, the angled linker may be capable of imparting an angle of less than about 155° in at least one orientation.

For six-membered rings, such angles can be achieved through ortho or meta linkages to the rest of the polymer. For five-membered rings, adjacent linkages fall within this range. For eight-membered rings, linkages extending from adjacent ring atoms, from alternate ring atoms (separated by one ring atom), and from ring atoms separated by two other ring atoms fall within this range. Ring systems with more than eight ring atoms may be used. For polycyclic structures, even more diverse linkage angles can be achieved.

Exemplary linking units which meet these limitations include benzene derivatives incorporated into the polymer in the 1, 2 or 1,3-positions; naphthalene derivatives incorporated into the polymer in the 1,2-, 1,3-, 1,6-, 1,7-, 1,8-positions; anthracene derivatives incorporated into the polymer in the 1,2-, 1,3-, 1,6-, 1,7-, 1,8-, and 1,9-positions; biphenyl derivatives incorporated into the polymer in the 2,3-, 2,4-, 2,6-, 3,3'-, 3,4-, 3,5-, 2,2'-, 2,3'-, 2,4'-, and 3,4'-positions; and corresponding heterocycles. The position numbers are given with reference to unsubstituted carbon-based rings, but the same relative positions of incorporation in the polymer are encompassed in substituted rings and/or heterocycles should their distribution of substituents change the ring numbering.

The CP in some cases contains at least 0.01 mol % of the angled linker, and may contain at least 0.02 mol %, at least 0.05 mol %, at least 0.1 mol %, at least 0.2 mol %, at least 0.5 mol %, at least 1 mol %, at least 2 mol %, at least 5 mol %, at least 10 mol %, at least 20 mol %, or at least 30 mol %. The CCP may contain up to 100 mol % of the angled linker, and may contain 99 mol % or less, 90 mol % or less, 80 mol % or less, 70 mol % or less, 60 mol % or less, 50 mol % or less, or 40 mol % or less.

The CP can be a copolymer, and may be a block copolymer, a graft copolymer, or both. The angled linker may be incorporated into the CP randomly, alternately, periodically and/or in blocks. In one aspect, the angled linker can be selected from aromatic or heteroaromatic structures in which the shortest link between the linking points to the polymer involves an even number of atoms bonded to one another.

In some instances, the conformationally flexible CPs are water soluble, and any or all of the subunits of the polymer may comprise one or more water soluble groups, including the angled linker(s).

Synthesis of Conjugated Polymers

A synthetic approach of interest is as follows. A neutral conjugated polymer is formed by the Suzuki coupling of a targeted ratio of monomer units, to produce a neutral conjugated polymer that may include heteroalkyl substituents. For example, as depicted in example, Schemes 2 and 3, 1,3-phenylenebisboronic acid and/or 1,4-phenylenebisboronic acid may be coupled with 2,7-dibromo-9,9-bis(6'-bromohexyl)fluorene to produce a substituted neutral CP. In some embodiments, the heteroalkyl substituted conjugated polymer may be further derivatized with any convenient group. In some instances, a water-soluble conjugated polymer is produced by inclusion of a water soluble group in a monomeric unit during polymer synthesis. In certain instances, a water soluble group is included via derivatization of a CP after polymer synthesis. For example, a water soluble group may be added via derivatization of a 6'-bromohexyl substituted CP.

The Signaling Chromophore

Chromophores useful in the inventions described herein include any substance which can absorb energy from a light harvesting multichromophore, when it is configured in energy-receiving proximity to the multichromophore and emit light. Chemical methods for attaching (e.g., directly or indirectly) a signaling chromophore to a sensor molecule and/or another assay component, such as a light harvesting multichromophore, are known.

The chromophore may be a lumophore or a fluorophore. Fluorophores of interest include, but are not limited to, fluorescent dyes, semiconductor nanocrystals, lanthanide chelates, and green fluorescent protein. Exemplary fluorescent dyes include, but are not limited to, fluorescein, 6-FAM, rhodamine, Texas Red, tetramethylrhodamine, a carboxyrhodamine, carboxyrhodamine 6G, carboxyrhodol, carboxyrhodamine 110, Cascade Blue, Cascade Yellow, coumarin, Cy2®, Cy3®, Cy3.5®, Cy5®, Cy5.5®, Cy-Chrome, phycoerythrin, PerCP (peridinin chlorophyll-a Protein), PerCP-Cy5.5, JOE (6-carboxy-4',5'-dichloro-2',7'-dimethoxyfluorescein), NED, ROX (5-(and-6)-carboxy-X-rhodamine), HEX, Lucifer Yellow, Marina Blue, Oregon Green 488, Oregon Green 500, Oregon Green 514, Alexa Fluor® 350, Alexa Fluor® 430, Alexa Fluor® 488, Alexa Fluor® 532, Alexa Fluor® 546, Alexa Fluor® 568, Alexa Fluor® 594, Alexa Fluor® 633, Alexa Fluor® 647, Alexa Fluor® 660, Alexa Fluor® 680, 7-amino-4-methylcoumarin-3-acetic acid, BODIPY® FL, BODIPY® FL-Br$_2$, BODIPY® 530/550, BODIPY® 558/568, BODIPY® 564/570, BODIPY® 576/589, BODIPY® 581/591, BODIPY® 630/650, BODIPY® 650/665, BODIPY® R6G, BODIPY® TMR, BODIPY® TR, conjugates thereof, and combinations thereof. Exemplary lanthanide chelates include europium chelates, terbium chelates and samarium chelates.

A wide variety of fluorescent semiconductor nanocrystals ("SCNCs") are known in the art and may find use as a signalling chromophore; methods of producing and utilizing semiconductor nanocrystals are described in: PCT Publ. No. WO 99/26299 published May 27, 1999, inventors Bawendi et al.; U.S. Pat. No. 5,990,479 issued Nov. 23, 1999 to Weiss et al.; and Bruchez et al., Science 281:2013, 1998. Semiconductor nanocrystals can be obtained with very narrow emission bands with well-defined peak emission wavelengths, allowing for a large number of different SCNCs to be used as signaling chromophores in the same assay, optionally in combination with other non-SCNC types of signaling chromophores. In some cases, the signaling chromophore is a polynucleotide-specific dye such as an intercalating dye. Other dyes and fluorophores of interest are described at www.probes.com (Molecular Probes, Inc.).

In some cases, the signaling chromophore is a fluorescent protein, such as a green fluorescent protein (GFP). The term "green fluorescent protein" refers to both native *Aequorea* green fluorescent protein and mutated versions that have been identified as exhibiting altered fluorescence characteristics, including altered excitation and emission maxima, as well as excitation and emission spectra of different shapes (Delgrave, S. et al. (1995) Bio/Technology 13:151-154; Heim, R. et al. (1994) Proc. Natl. Acad. Sci. USA 91:12501-12504; Heim, R. et al. (1995) Nature 373:663-664). Delgrave et al. isolated mutants of cloned *Aequorea Victoria* GFP that had red-shifted excitation spectra. Bio/Technology 13:151-154 (1995). Heim, R. et al. reported a mutant (Tyr66 to His) having a blue fluorescence (Proc. Natl. Acad. Sci. (1994) USA 91:12501-12504).

For multiplexed assays, a plurality of different signaling chromophores can be used with detectably different emission spectra. In some embodiments, a second signaling chromophore may be directly or indirectly attached to another of the assay components and/or to a substrate. In certain instances, the second signaling chromophore is used to receive energy from the initial signaling chromophore. In certain instances, this configuration can provide for significant additional selectivity. Energy can then be transferred from the excited light harvesting multichromophore to the initial signaling chromophore, which subsequently transfers energy to the second signaling chromophore, in an overall format that provides for detection of the target. This cascade of signaling chromophores can, in principle, be extended to use any number of signaling chromophores with compatible absorption and emission profiles.

Sensor Molecules

In some instances, a sensor molecule is provided that is complementary to the target to be detected. Any convenient sensor molecules that are complementary to a target may be utilized in the subject compositions and methods. Sensor molecules of interest include biomolecules, including but not limited to, a peptide or protein, a polynucleotide such as DNA or RNA, and an antibody. In certain embodiments, the sensor biomolecule is an antibody. In some cases, the sensor molecule is attached to a signaling chromophore. A variety of chemical methods for attaching a signaling chromophore to sensor are known in the art. Specific sensor structures, including structures conjugated to chromophores, can be custom-made using commercial sources or chemically synthesized.

In some embodiments, the sensor molecule is a sensor PNA that is complementary to a target polynucleotide to be assayed, and has a predetermined sequence. In certain embodiments, the sensor PNA can be branched, multimeric or circular, but is in some cases linear, and can contain nonnatural bases. The molecular structures of PNAs are well known. PNAs can be prepared with any desired sequence of bases. Chemical methods for attaching the signaling chromophore to the sensor PNA are well known. Specific sensor PNA structures, including structures conjugated to chromophores, can be custom-made using commercial sources or chemically synthesized.

In some instances, the sensor molecule is a sensor polynucleotide that is complementary to a target polynucleotide to be assayed, and has a predetermined sequence. The sensor polynucleotide can be branched, multimeric or circular, but is in some cases linear, and can contain nonnatural bases. The sensor polynucleotide can be prepared with any desired sequence of bases. Chemical methods for attaching the signaling chromophore to the sensor polynucleotide are known in the art. Specific sensor polynucleotide structures, including structures conjugated to chromophores, can be custom-made using commercial sources or chemically synthesized.

In some cases, the sensor molecule is a peptide or protein, e.g., a target binding protein. Any protein sensor molecule which can specifically bind to a target polynucleotide of interest can be employed in the compositions and methods disclosed. In some embodiments, the target binding protein is an antibody that specifically binds a target biomolecule. In certain embodiments, the target binding protein is a sensor polynucleotide binding protein (PBP) that specifically binds to a target polynucleotide to be assayed.

Protein biomolecules that find use as a sensor molecule for specifically binding a target biomolecule in the subject compositions and methods may be prepared using any convenient methods. In some cases, the protein sensor molecule is synthesized by the solid phase method and/or can be purified by HPLC and/or characterized by MALDI-TOF mass spectrum and amino acid analysis. The chemical methods for attaching a signaling chromophore to a protein sensor molecule are known. A specific example is the labelling composition including Tat-C* with fluorescein at the N-terminus.

Non-limiting examples of target binding proteins include, but are not limited to, transcription factors, splicing factors, poly(A) binding proteins, chromatin components, viral proteins, proteins which detect viral infection, replication factors, and proteins involved in mitotic and/or meiotic cell division. Examples of specific sensor proteins which can be used include Tat which binds to the Rev Responsive Element of human immunodeficiency virus (HIV), the matrix protein M1 which binds to Type A influenza virus RNA, and hnRNP U protein which binds to pre-ribosomal RNA.

Compositions

Aspects of the invention include compositions for detecting a target that include a signaling chromophore configured in energy-receiving proximity to a light harvesting multichromophore, such that amplification of the emission from the signaling chromophore occurs. The subject compositions include light harvesting multichromophores that are configured so that they can interact with a signaling chromophore which is in energy-receiving proximity therewith by virtue of any convenient connection. In some embodiments, the connection is an indirect connection via a sensor molecule. In some instances, the subject composition is utilized as a detection reagent in an assay to directly label a target biomolecule.

The proximity between a signaling chromophore and a light harvesting and luminescent multi-chromophore system may be ensured by any convenient connection. Terms such as "connected," "attached," "linked" and conjugated are used interchangeably herein and encompass direct as well as indirect connection, attachment, linkage or conjugation unless the context clearly dictates otherwise. Any convenient connection, attachment, linkage or conjugation of the signaling chromophore in energy-receiving proximity to the light harvesting multichromophore may provide for optical amplification via Förster energy transfer. The signaling chromophore may be connected directly or indirectly to the light harvesting multichromophore. In some embodiments, the signaling chromophore and the light harvesting multichromophore may be connected in a detection reagent prior to assaying a sample for the presence of a target.

In some cases, the connection between the light harvesting multichromophore and the signaling chromophore is indirect, e.g., is achieved by virtue of a binding event. In certain instances, the connection between the light harvesting multichromophore and the signaling chromophore is direct, e.g., via covalent bonds. In some instances, the connection between the light harvesting multichromophore and the signaling chromophore is direct and is achieved by virtue of a direct linkage or conjugation. In certain embodiments, the light harvesting multichromophore and the signaling chromophore may be attached to a sensor molecule.

Aspects of the invention include labelling compositions that include a signaling chromophore and a light harvesting multichromophore. As used herein, the terms "labelling composition" and "detection reagent" are used interchangeably, and refer to a composition that finds use in labelling and detecting a target analyte. When the average distance between the light harvesting multichromophore and the signaling chromophore is too large for effective energy transfer, there is little or no emission from the signaling chromophore. As such, the light harvesting multichromophore may be configured upon excitation to transfer energy to, and amplify the emission from, an acceptor signaling chromophore in energy-receiving proximity therewith.

It is understood that any convenient components and methods may be utilized in connecting the light harvesting multichromophore and the signaling chromophore to provide a labelling composition, as long as those components and methods permit energy transfer from the light harvesting multichromophore to the signaling chromophore in the labelling composition, for example via the Förster energy transfer mechanism. In some cases, the connection between the light harvesting multichromophore and the signaling chromophore is achieved where a signaling chromophore is conjugated to a sensor molecule that is also associated with a light harvesting multichromophore, where the sensor molecule has affinity for the target analyte. Under these circumstances, the connection between the signaling chromophore and the light harvesting multichromophore system is achieved, leading to efficient energy transfer and intense emission from the signaling chromophore. As such, it is understood that the signaling chromophore should be in energy-receiving proximity with the light harvesting multichromophore to achieve optical amplification in the labelling composition. Such energy-receiving proximity may be achieved by virtue of any convenient direct or indirect connection. It is understood that the target analyte may be labelled with the light harvesting multichromophore and an acceptor signaling chromophore in energy-receiving proximity therewith.

The subject compositions including a signaling chromophore and a light harvesting multichromophore may further include one or more components. In some cases, the composition includes a signaling chromophore, a light harvesting multichromophore and a sensor molecule that specifically binds a target.

In some instances, the invention provides a predominantly aqueous solution including a light harvesting multichromophore, a sensor molecule and a signaling chromophore. In certain embodiments, the sensor molecule is conjugated to the signaling chromophore. In certain cases, the sensor molecule is conjugated to the light harvesting multichromophore. In certain cases, the signaling chromophore is conjugated to the light harvesting multichromophore. In certain embodiments, the light harvesting multichromophore is conjugated to the signaling chromophore and the sensor molecule.

In some embodiments, the invention provides a predominantly aqueous solution comprising a light harvesting multichromophore (e.g., a CP), a "sensor biomolecule" and a signaling chromophore. In certain embodiments, the light harvesting multichromophore is conjugated to the signaling chromophore and the sensor molecule.

As discussed herein, the optical amplification provided by a water soluble light harvesting multichromophore can be used to detect a target analyte. In some cases, the amplification can be enhanced by using higher molecular weight water soluble conjugated polymers or other structures as the light harvesting multichromophore. The invention can be provided in a homogeneous format that utilizes the ease of fluorescence detection methods. Amplification of the emission from the acceptor signaling chromophore may occur when incident light is at a wavelength absorbed by the donor light harvesting multichromophore system as compared to when the acceptor signaling chromophore is directly excited by incident light, e.g., at the absorbance maximum of the acceptor. In certain embodiments, the amplification of the emission from the acceptor signaling chromophore is 2-fold greater or more, such as 3-fold greater or more, 4-fold greater or more, 6-fold greater or more, 8-fold greater or more, 10-fold greater or more, 15-fold greater or more, 25-fold greater or more, 30-fold greater or more, or even more as compared to when the acceptor signaling chromophore is directly excited by incident light.

In some embodiments of the compositions and methods, the ratio of the donor light harvesting multichromophore to the acceptor signaling chromophore is 1:1. In certain instances, the donor light harvesting multichromophore includes a conjugated polymer of aromatic repeat units and the ratio of the number of repeat units to the acceptor signaling chromophore is 100:1 or more.

Methods of Use

Aspects of the invention include contacting a sample with a predominantly aqueous composition including: (a) a light harvesting, luminescent multichromophore system such as, for example, a conjugated polymer, semiconductor quantum dot or dendritic structure that is water soluble; and (b) a sensor molecule conjugated to a luminescent signaling chromophore C*. The emission of a wavelength of light characteristic of the signaling chromophore-C* upon excitation of the light harvesting multichromophore may be used to detect the target. In some embodiments, the emission of the signaling chromophore is used to detect the sensor molecule-target complex.

The light harvesting multichromophores may be used in methods which screen the light harvesting multichromophores for any property of interest. For example, the light harvesting multichromophores may be tested for energy transfer to a chromophore, for increased fluorescent efficiency, for decreased self-quenching, for absorbance wavelength, and/or for emission wavelength.

A sensor molecule that is specific for the target may be used in conjugation with the light harvesting multichromophores, as can a signaling chromophore to which energy may be transferred from the light harvesting multichromophores. In certain instances, a sensor molecule of known structure is used to label the target in the sample. The sensor molecule may provide a signal specific to its complementary target in any of various ways, e.g., through incorporation of a specific signaling chromophore which can receive energy from the light harvesting multichromophore (e.g. CP). The signaling chromophore may be incorporated into the sensor molecule, or in some cases, may be recruited to a complex formed from the sensor molecule and the target. Formation of such a complex results in an increase of energy transfer from a light harvesting multichromophore upon excitation to the signaling chromophore, which may be detected directly or indirectly to provide information regarding the target.

The compositions described herein are useful for any assay in which a sample can be interrogated regarding a target biomolecule. In some embodiments, the assays involve determining the presence of the target in the sample or its relative amount, or the assays may be quantitative or semi-quantitative. As such, provided are methods of determining whether a target in present in a sample. In some embodiments, the method includes: contacting the sample with: a labelling composition (e.g., as described herein) to produce a labelling composition contacted sample; and assaying the labelling composition contacted sample for the presence of fluorescently labeled target analyte to evaluate whether the target analyte is present in the sample. Also provided are methods of detecting a target in a sample. In some instances, the method includes: contacting the sample with a labelling composition (e.g., as described herein) to produce a labelled target; and detecting the labelled target. The methods of the invention can all be performed in multiplex formats. A plurality of different sensor biomolecules can be used to detect corresponding different target biomolecules in a sample through the use of different signaling chromophores conjugated to the respective sensor biomolecules. In some cases, the light harvesting multichromophore (e.g., as described herein) is connected to the sensor biomolecule to provide for amplification of the signaling chromophore. Multiplex methods are provided employing 2, 3, 4, 5, 10, 15, 20, 25, 50, 100, 200, 400 or more different sensor biomolecules which can be used simultaneously to assay for corresponding different target biomolecules. The subject methods and compositions can be performed or utilized on a substrate, as well as in solution.

Any target molecule and any sensor molecule that can bind to each other can in principle be used in conjunction with the subject methods, where the light harvesting multichromophore may be associated with the sensor molecule. In some cases, this attachment may be accomplished through any convenient means to configure the light harvesting multichromophore in signaling juxtaposition with the signaling chromophore. In certain instances, the light harvesting multichromophore is attached to the sensor molecule in signaling juxtaposition to the signaling chromophore, where the sensor molecule specifically binds the target.

Targets

The target molecule may be a biomolecule, for example a peptide or protein, a polynucleotide such as DNA or RNA, and an antibody. Similarly, sensor molecules of interest include biomolecules. Exemplary sensor biomolecules of interest include, but are not limited to, a polynucleotide, a peptide nucleic acid (PNA), an antibody, a peptide or a protein.

Samples

Where the target is present in a biological sample, the portion of the sample comprising or suspected of comprising the target can be any source of biological material that can be obtained from a living organism directly or indirectly, including cells, tissue or fluid, and the deposits left by that organism, including viruses, mycoplasma, and fossils. The sample may comprise a target prepared through synthetic means, in whole or in part. Typically, the sample is obtained as or dispersed in a predominantly aqueous medium. Non-limiting examples of the sample include blood, urine, semen, milk, sputum, mucus, a buccal swab, a vaginal swab, a rectal swab, an aspirate, a needle biopsy, a section of tissue obtained for example by surgery or autopsy, plasma, serum, spinal fluid, lymph fluid, the external secretions of the skin, respiratory, intestinal, and genitourinary tracts, tears, saliva, tumors, organs, samples of in vitro cell culture constituents (including but not limited to conditioned medium resulting from the growth of cells in cell culture medium, putatively virally infected cells, recombinant cells, and cell components), and a recombinant library comprising polynucleotide sequences.

The sample can be a positive control sample which is known to contain the target or a surrogate therefor. A negative control sample can also be used which, although not expected to contain the target, is suspected of containing it (via contamination of one or more of the reagents) or another component capable of producing a false positive, and is tested in order to confirm the lack of contamination by the target of the reagents used in a given assay, as well as to determine whether a given set of assay conditions produces false positives (a positive signal even in the absence of target in the sample).

The sample can be diluted, dissolved, suspended, extracted or otherwise treated to solubilize and/or purify any target present or to render it accessible to reagents, e.g., to detection reagents. Where the sample contains cells, the cells can be lysed or permeabilized to release the target within the cells.

Substrates

The methods described herein can be performed on a substrate in any of a variety of formats. One or more of the assay components may be incorporated in, attached to, or otherwise associated with the substrate, directly or indirectly. The substrate can comprise a wide range of materials, such as biological, nonbiological, organic, inorganic, or a combination of any of these.

Excitation and Detection of the Chromophores

Any convenient instrument that provides a wavelength that can excite the light harvesting multichromophore and is shorter than the emission wavelength(s) to be detected can be used for excitation. The excitation source in some cases does not significantly excite the signaling chromophore directly. The source may be: a broadband UV light source such as a deuterium lamp with an appropriate filter, the output of a white light source such as a xenon lamp or a deuterium lamp after passing through a monochromator to extract out the desired wavelengths, a continuous wave (cw) gas laser, a solid state diode laser, or any of the pulsed lasers. The emitted light from the signaling chromophore can be detected through any convenient device or technique. For example, a fluorimeter or spectrophotometer may be used to detect whether the test sample emits light of a wavelength characteristic of the signaling chromophore upon excitation of the multichromophore.

Kits

Kits comprising reagents useful for performing the methods of the invention are also provided. In one embodiment, a kit comprises a sensor molecule (e.g., as described herein) that specifically binds to a target molecule of interest and a light harvesting multichromophore (e.g., as described herein). The sensor molecule may be conjugated to a signaling chromophore. In certain instances, the sensor molecule is a protein. In certain embodiments, the light harvesting multichromophore is a conjugated polymer (CP).

The signaling chromophore may be configured in energy receiving proximity to the light harvesting multichromophore. In the presence of the target in the sample, the sensor molecule binds to the target which can be detected. The fluorescence detected includes increased emission of energy from the signaling chromophore.

The components of the kit can be retained by a housing. Instructions for using the kit to perform a method of the invention can be provided with the housing, and can be provided in any fixed medium. The instructions may be located inside the housing or outside the housing, and may be printed on the interior or exterior of any surface forming the housing which renders the instructions legible. The kit may be in multiplex form, containing pluralities of one or more different sensor molecules (e.g., PNAs) which can bind (e.g., hybridize) to corresponding different target molecules (e.g., target polynucleotides).

EXAMPLES

The following examples are set forth so as to provide those of ordinary skill in the art with a complete description of how to make and use the present invention, and are not intended to limit the scope of what is regarded as the invention. Efforts have been made to ensure accuracy with respect to numbers used (e.g., amounts, temperature, etc.) but some experimental error and deviation should be accounted for. Unless otherwise indicated, parts are parts by weight, temperature is degree centigrade and pressure is at or near atmospheric, and all materials are commercially available.

Example 1: PNA Sensor Molecules

Example 1-1: Identification of a Multichromophore/Signaling Chromophore Pair for FRET The ability to transfer energy from the light harvesting multichromophore system to the signaling chromophore on a sensor PNA was demonstrated using the water soluble conjugated polymer poly((9,9-bis(6'-N,N,N-trimethylammonium)-hexyl)-fluorene phenylene), polymer 1 with iodide counteranions, and the sensor peptide nucleic acid PNA-C* having the sequence 5'-CAGTCCAGTGATACG-3' and conjugated to fluorescein (C*) at the 5' position. Excitation was performed at 380 and 480 nm for 1 and PNA-C*, respectively. The data show that there is an optical window for the specific excitation of polymer 1. Moreover, there is excellent overlap between the emission of polymer 1 and the absorption of C* to allow FRET.

Example 1-2: Demonstration of Amplified Fluorescence Via FRET Between Light Harvesting Multichromophore and Signaling Chromophore in Complex with Target The PNA-C* probe ([PNA-C*]=2.5×10$^{-8}$ M) was contacted with an equimolar amount of the complementary 15 base pair ssDNA, (5'-CGTATCACTGGACTG-3')(SEQ ID NO:), and in an identical fashion with a non-complementary 15 base ssDNA, (5'-ACTGACGATAGACTG-3') (SEQ ID NO:), in separate vessels in the absence of polymer 1. The annealing step was performed in the absence of buffer, i.e. at low ionic strength, at 2° C. below the T$_m$ of PNA-C* (72° C. at 10$^{-8}$M, pH=5.5). A melting experiment was performed and the absorbance monitored by UV/Vis spectroscopy at 260 nm. Increasing the temperature led to an increase in absorbance upon melting of the hybridized duplex in the sample containing the complementary ssDNA, as the two single strands absorb more highly than the hybridized duplex. As expected, the sample containing the non-complementary ssDNA did not show such an increase in absorbance, as no duplex was formed in that sample.

FRET was measured in annealed samples containing the complementary and non-complementary ssDNAs and polymer 1 ([1]=2.3×10$^{-7}$ M). The normalized emission spectra of PNA-C* in the presence of complementary and non-complementary DNA upon excitation of polymer 1 are shown in FIG. 1. A FRET ratio >11 times higher for the PNA/DNA hybrid was detected, relative to the non-complementary pair. The fluorescein emission was more than 8 times larger than that obtained from direct C* excitation in the absence of 1. This increased C* emission in the energy transfer complex indicates that optical amplification is provided by the multichromophore (polymer 1).

Example 2: Polynucleotide Sensor Molecules

Example 2-1: Identification of FRET Between Light Harvesting Multichromophore and Signalling Chromophore Energy transfer from the light harvesting multi-chromophore system to the signaling chromophore was demonstrated using the water soluble conjugated polymer poly(9,9-bis(6'-N,N,N-trimethylammonium)-hexyl)-fluorene phenylene), polymer 1 with iodide counteranions. The sensor polynucleotide sequence was 5'-GTAAATGGTGT-TAGGGTTGC-3' (SEQ ID NO:), corresponding to the anthrax (Bacillus anthracis) spore encapsulation plasmid, pX02, with fluorescein at the 5' position, forming an example of oligo-C*. The data shows an optical window for the excitation of polymer 1, between the absorption of DNA and fluorescein. Direct excitation of polymer 1 results in energy transfer (ET) to fluorescein. The absorbance overlap of fluorescein with the emission of polymer 1 was selected to ensure FRET. The extent of ET is evaluated by the ratio of integrated acceptor to donor emission.

Example 2-2 Demonstration of Amplified Fluorescence Via FRET Between Light Harvesting Multichromophore and Signalling Chromophore in a Complex with a Target The sensor polynucleotide ([Oligo-C*]=$2.1\times10^{-8}$ M) was annealed at 2° C. below its $T_m$ (58.4° C.) in the presence of an equal molar amount of a 40 base pair strand containing a complementary 20 base pair sequence, 5'-CATCTGTAAATCCAAGAGTAGCAACCCTAACACCATTTAC-3' (SEQ ID NO:), and in an identical fashion with a non-complementary 40 base strand with the sequence 5'-AAAATATTGTGTATCAAAATGTAAATGGTGTTAGGGTTGC-3' (SEQ ID NO:). Direct comparison of the resulting fluorescence reveals an ET ratio greater than 6 fold higher for the hybridized DNA. Using a Xenon lamp fluorometer, equipped with a standard PMT, the hybridized DNA provided over 3 fold greater ET ratios, at [sensor polynucleotide]=$2.8\times10^{-9}$M, than did the non-hybridized DNA.

Example 2-3: FRET Transfer to a Target Specific Dye

Experiments using 1 and ethidium bromide ("EB") as a signaling chromophore demonstrate that direct energy transfer from 1 to EB could be shown in the presence of double-stranded DNA. The sensor polynucleotide (5'-ATCTTGACTATGTGGGTGCT-3') (SEQ ID NO:) lacking the signaling chromophore ([Oligo]=$1\times10^{-8}$ M) was annealed at 2° C. below its $T_m$ (58.5° C.) in the presence of an equal molar amount of a 20 base pair strand containing a complementary 20 base pair sequence, (5'-AGCACCCACATAGTCAAGAT-3') (SEQ ID NO:), and in an identical fashion with a non-complementary 20 base pair strand with the sequence (5'-CGTATCACTGGACTGATTGG-3') (SEQ ID NO:). The two DNA mixtures were mixed with Ethidium Bromide ([EB]=$1.1\times10^{-6}$ M) at room temperature in potassium phosphate monobasic-sodium hydroxide buffer solution (50 mM, pH=7.40) where the intercalation of the EB occurred within the duplex structure of the hybridized DNA pair. Addition of polymer 1 in water ([1]=$1.6\times10^{-7}$ M) and subsequent excitation of 1 (380 nm) resulted in energy transfer from 1 to the intercalated EB only in the case of hybridized or double stranded DNA.

Example 3: Protein Sensor Molecules

The TAR RNA and dTAR RNA oligonucleotides described below were purchased from Dharmacon Research Inc. (Lafayette, USA). The polypeptides modified by fluorescein on the N-terminus (Tat-C* and SH3-C*) were custom-made by Sigma-Genosys (Texas, USA). All the fluorescence and FRET experiments were carried out using a PTI Quantum Master fluorometer equipped with a Xenon lamp excitation source in tris-EDTA buffer solution (10 mM, pH=7.4).

Example 3-1

Emission spectra and absorption spectra were obtained to show that there is excellent overlap between the emission of polymer 1 and the absorption of Tat-C* to ensure fluorescence resonance energy transfer.

Example 3-2

Emission spectra and absorption spectra were obtained to show that there is excellent overlap between the emission of oligomer 1 and the absorption of Tat-C* to ensure fluorescence resonance energy transfer.

Example 3-3

Emission spectra and absorption spectra were obtained to show that there is excellent overlap between the emission of oligomer 2 and the absorption of Tat-C* to ensure fluorescence resonance energy transfer.

Example 3-4

The Tat-C* probe ([Tat-C*]=1.0×10$^{-8}$ M) was mixed with an equimolar amount of the TAR RNA at room temperature, and in an identical fashion with a non-specific dTAR RNA. It is known that a bulge structure in TAR RNA is a requirement for Tat peptide binding to TAR RNA. dTAR RNA is closely related in structure to TAR RNA, lacking the three base bulge structure necessary for Tat binding.

Addition of oligomer 1 in water ([oligomer 1]=8.0×10$^{-8}$ M) and subsequent comparison of the resulting fluorescence of Tat-C* obtained by excitation at 365 nm reveals an intensity ratio >10 times higher for the Tat-C*/TAR RNA, relative to the non-specific Tat-C*/dTAR RNA pair. The fluorescein emission is more than 25 times larger than that obtained from direct Tat-C* excitation at the absorption maximum of fluorescein in the absence of oligomer 1. The increased Tat-C* emission in the energy transfer complex indicates that optical amplification is provided by the conjugated oligomer 1.

Example 3-5

The Tat-C* probe ([Tat-C*]=1.0×10$^{-8}$ M) was mixed with an equimolar amount of the TAR RNA at room temperature, and in an identical fashion with a non-specific dTAR RNA. Addition of oligomer 2 in water ([oligomer 2]=6.0×10$^{-8}$M) and subsequent comparison of the resulting fluorescence of Tat-C* obtained by excitation at 375 nm reveals an intensity ratio 15 times higher for the Tat-C*/TAR RNA, relative to the non-specific Tat-C*/dTAR RNA pair. The fluorescein emission is more than 30 times larger than that obtained from direct Tat-C* excitation in the absence of oligomer 2. The increased Tat-C* emission in the energy transfer complex indicates that optical amplification is provided by the conjugated oligomer 2.

Example 3-6

The water soluble conjugated polymer 1 (average n=app. 15) was utilized to as the light harvesting chromophore. The Tat-C* probe ([Tat-C*]=1.0×10$^{-8}$ M) was mixed with an equimolar amount of the TAR RNA at room temperature, and in an identical fashion with a non-specific dTAR RNA. Addition of polymer 1 in water ([polymer 1]=4.8×10$^{-7}$ M) into the mixture of Tat-C* and TAR RNA results in fluorescence of Tat-C* with an intensity ratio >15 times higher than that of the non-specific Tat-C*/dTAR RNA and 10 times larger than that obtained from direct Tat-C* excitation in the absence of polymer 1. Thus, significantly higher FRET ratios and correspondingly higher sensitivities can be achieved.

Example 3-7

Another peptide sequence labeled with fluorescein at the N-terminus (SH3-C*; AKPRPPRPLPVAC in single letter code) (SEQ ID NO:) which cannot specifically bind to TAR RNA was also utilized as the signal molecule. The mixture of [SH3-C* or Tat-C*]=1.0×10$^{-8}$ M, [TAR RNA]=1.0×10$^{-8}$ M and [oligomer 1]=8.0×10$^{-8}$ M) shows C* emission only when the Tat-C* was present.

Example 4

Conjugated polymers were synthesized through the Suzuki coupling reaction and a post-polymerization quaternization step. Synthetic examples are given with respect to the specific polymers under Formula 1. The synthetic routes are shown in the Schemes below

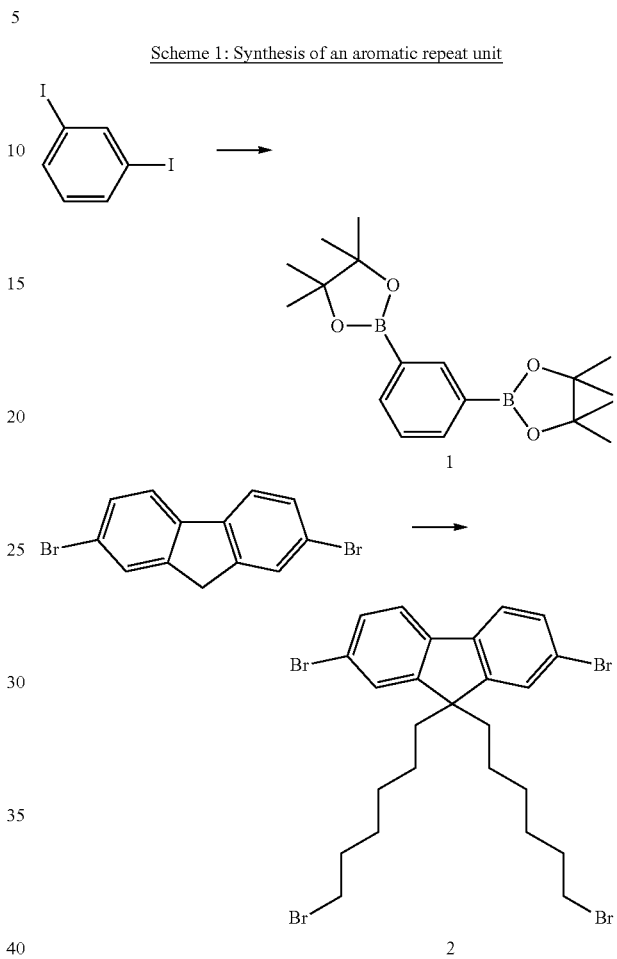

Scheme 1: Synthesis of an aromatic repeat unit

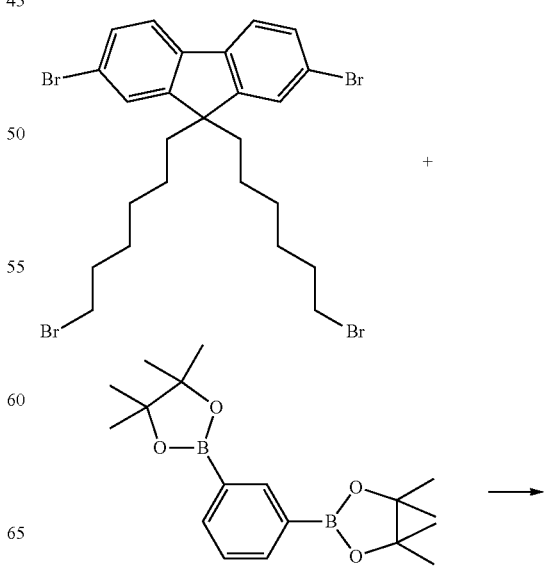

Scheme 2: Synthesis of a conjugated polymer

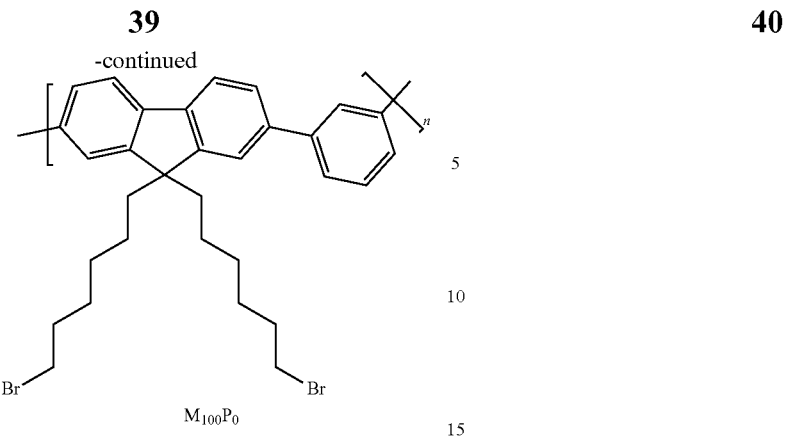
M₁₀₀P₀
Scheme 3: Synthesis of a conjugated polymer
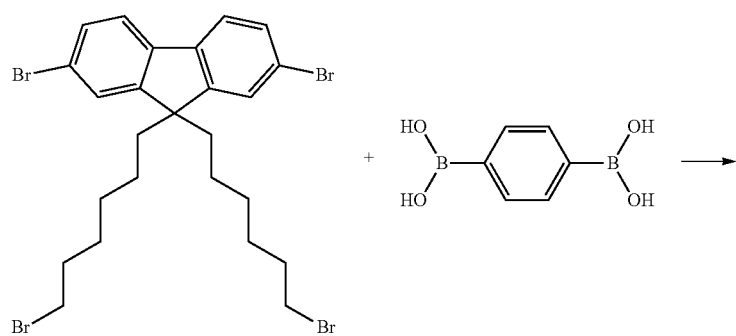
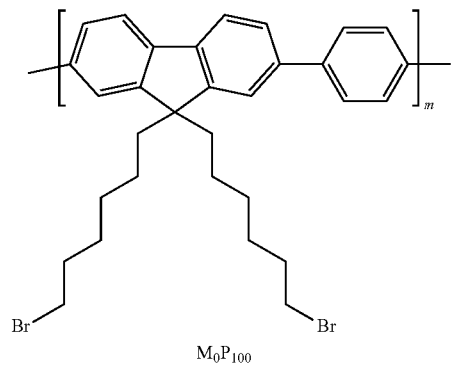
M₀P₁₀₀
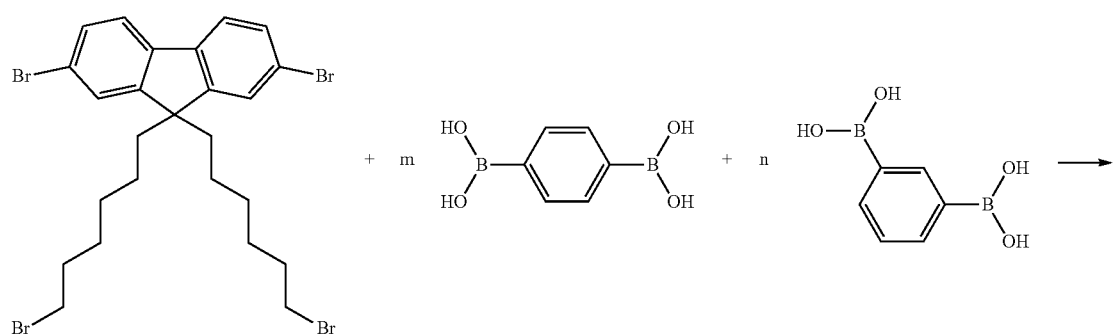

-continued

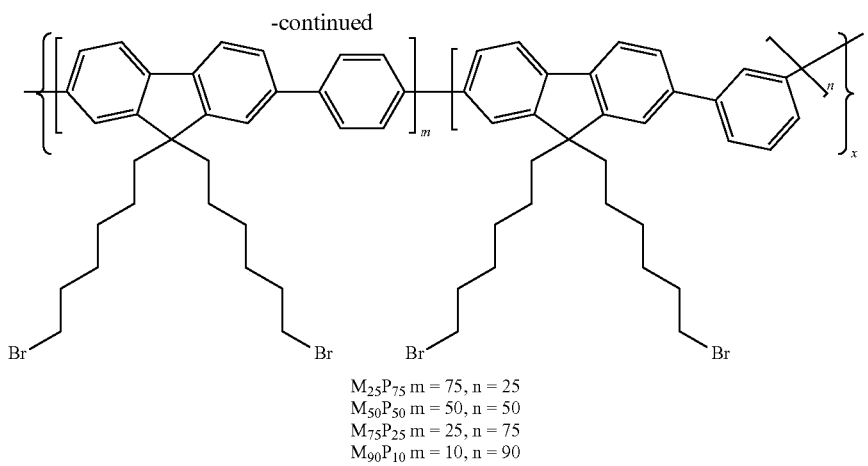

M$_{25}$P$_{75}$ m = 75, n = 25
M$_{50}$P$_{50}$ m = 50, n = 50
M$_{75}$P$_{25}$ m = 25, n = 75
M$_{90}$P$_{10}$ m = 10, n = 90

Scheme 4: Derivatization of a conjugated polymer

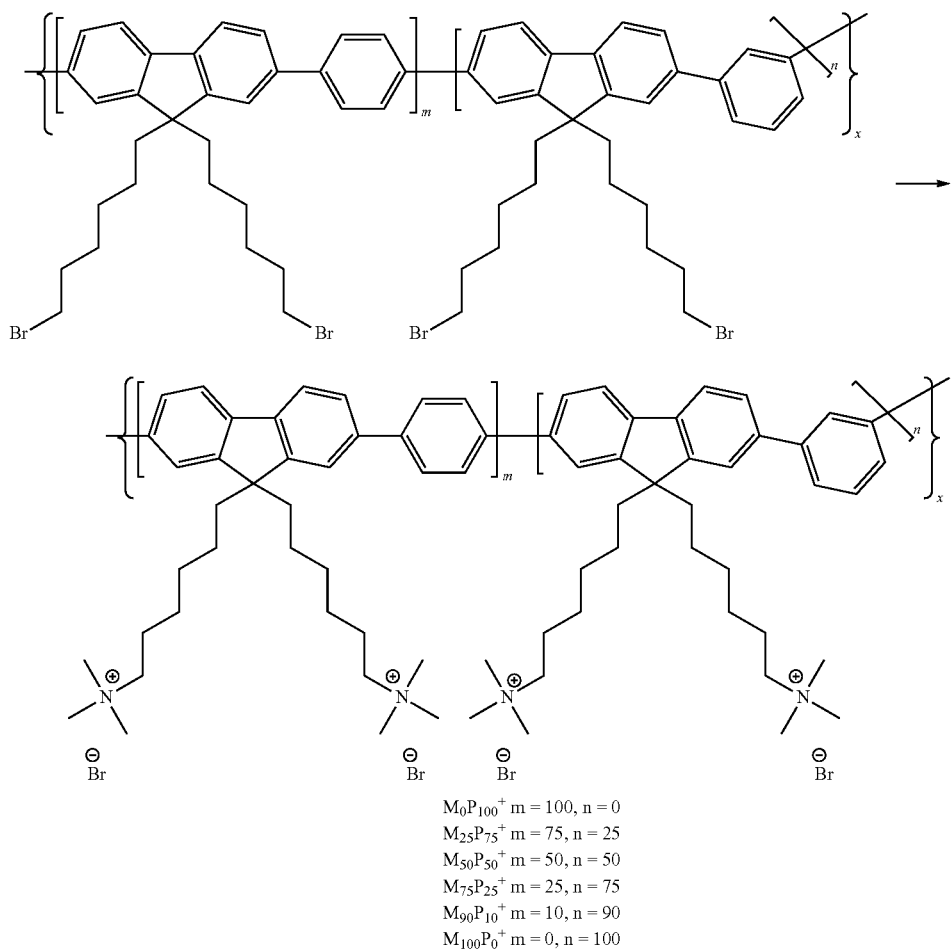

M$_{0}$P$_{100}^+$ m = 100, n = 0
M$_{25}$P$_{75}^+$ m = 75, n = 25
M$_{50}$P$_{50}^+$ m = 50, n = 50
M$_{75}$P$_{25}^+$ m = 25, n = 75
M$_{90}$P$_{10}^+$ m = 10, n = 90
M$_{100}$P$_{0}^+$ m = 0, n = 100

An overview of the methods depicted in Schemes 1-4 is as follows. 1,3-Bis(4,4,5,5-tetramethyl-1,3,2-dioxaborolan)phenylene (1) was obtained in 46% yield by treating 1,3-diiodobenzene with bis(pinacolato)diborane in the presence of PdCl$_2$(dppf) and potassium acetate in DMSO. 2,7-Dibromo-9,9-bis(6'-bromohexyl)fluorene (2) was obtained by the treatment of 2,7-dibromofluorene with 50% KOH, followed by addition of excess of 1,6-dibromohexane in 85% yield. Coupling of one equivalent of the dibromide monomer with one net equivalent of diboronic acid or diboronic ester, under Suzuki coupling conditions using PdCl$_2$(dppf) in refluxing THF/H$_2$O for 24 h, followed by purification gave the desired polymers including bromo-substituted alkyl substituents in 39% to 88% yield. The products were thoroughly washed with methanol and acetone, and then dried in vacuum for 24 h. Formation of the trimethylamine derivatized polymers was achieved by stirring the polymers in condensed trimethylamine in a THF/H$_2$O solvent mixture for 24 h.

Example 4-1: 1,3-Bis(4,4,5,5,-tetramethyl-1,3,2-dioxaborolan)phenylene (1)

A flask charged with 1,3-diiodobenzene (1.0 g, 3 mmol), bis(pinacolato)diborane (2.3 g, 9 mmol), potassium acetate (2.1 g, 21 mmol), PdCl$_2$(dppf) (150 mg, 0.18 mmol), and 15 mL of anhydrous DMSO was degassed for 15 minutes. The mixture was stirred at 80° C. for 12 h, cooled to room temperature and then poured into 100 mL of ice water. The mixture was extracted with CHCl$_3$, and the combined organic layers were dried over anhydrous MgSO$_4$. After the solvent was evaporated, the residue was purified by chromatography using silica gel (Hexane:CHCl3=1:1) and then recrystallized from ethanol to afford 1 (460 mg, 46%) as a white solid. $^1$H NMR (200 MHz, CDCl3): δ 8.28 (s, 1H), 7.91-7.89 (d, 2H), 7.38 (t, 1H), 1.35 (s, 24H). $^{13}$C NMR (50 MHz, CDCl$_3$): δ 141.4, 137.8, 127.3, 83.9, 25.1.

Example 4-2: 2,7-Dibromo-9,9-bis(6'-bromohexyl)fluorene (2)

To a mixture of tetrabutylammonium bromide (300 mg, 9.3 mmol), aqueous potassium hydroxide (100 mL, 50%) and 1,6-dibromohexane (22.6 g, 92.6 mmol) was added 2,7-dibromofluorene at 75° C. After 15 minutes, the mixture was cooled down to room temperature, and extracted with CH$_2$Cl$_2$. The organic layer was washed with water, aqueous HCl, water and brine, dried over MgSO$_4$, and then concentrated. Unreacted 1,6-dibromohexane was distilled off. The residue was purified by silica gel column chromatography (Hexane:CHCl$_3$=9:1) and recrystallized from ethanol to give 2 (4.8 g, 80%) as a white solid. $^1$H NMR (200 MHz, CDCl$_3$): δ 7.2-7.4 (m, 6H), 3.12 (t, 4H), 1.75 (t, 4H), 1.5 (m, 4H), 1.0 (m, 8H), 0.4 (m, 4H). $^{13}$C NMR (50 MHz, CDCl$_3$): δ 152.3, 139.2, 130.5, 126.2, 121.7, 121.4, 55.7, 40.2, 34.1, 32.8, 29.1, 27.9, 23.6.

Example 4-3: Poly(9,9-bis(6'-bromohexyl)fluorene-co-alt-1,3-phenylene) ($M_{100}P_0$)

2,7-Dibromo-9,9-bis(6'-bromohexyl)fluorene (325 mg, 0.5 mmol), 1,3-bis(4,4,5,5-tetramethyl-1,3,2-dioxaborolan)phenylene (166 mg, 0.5 mmol), Pd(PPh3)4 (8 mg) and potassium carbonate (830 mg, 6 mmol) were placed in a 25 mL round bottle flask. A mixture of water (3 mL) and toluene (5 mL) was added to the flask. After degassing, the mixture was refluxed at 85° C. for 20 h, and then precipitated into methanol. The polymer was filtered and washed with methanol and acetone, and then dried in vacuum for 24 h to afford $M_{100}P_0$ (251 mg, 88%) as a light yellow solid. 1H NMR (200 MHz, CDCl$_3$): δ 7.9-7.6 (m, 10H), 3.3-3.2 (t, 4H), 2.1 (m, 4H), 1.7-1.6 (m, 4H), 1.3-1.2 (m, 8H), 0.8 (m, 4H). 13C NMR (50 MHz, CDCl$_3$): δ 152.1, 142.9, 140.9, 130.1, 129.5, 128.0, 126.8, 122.5, 120.9, 55.9, 40.9, 34.5, 33.3, 29.7, 28.5, 24.3. GPC (THF, polystyrene standard), Mw: 40,250 g/mol; Mn: 14,980 g/mol; PDI: 2.8. UV-vis (CHCl$_3$): λmax=337 nm; PL (CHCl$_3$): λmax=363 nm.

Example 4-4 Poly(9,9-bis(6'-bromohexyl)fluorene-co-alt-1,4-phenylene) ($M_0P_{100}$)

2,7-Dibromo-9,9-bis(6'-bromohexyl)fluorene (325 mg, 0.5 mmol), 1,4-phenylenebisboronic acid (82.9 mg, 0.5 mmol), Pd(dppf)Cl$_2$ (7 mg) and potassium carbonate (830 mg, 6 mmol) were placed in a 25 mL round bottle flask. A mixture of water (3 mL) and THF (6 mL) was added to the flask and degassed. The mixture was refluxed at 85° C. for 24 h, and then precipitated into methanol. The polymer was filtered and washed with methanol and acetone, and then dried in vacuum for 24 h to afford M0P100 (220 mg, 78%) as an off-white solid. $^1$H NMR (200 MHz, CDCl3): δ 7.8 (m, 5H), 7.7-7.6 (m, 4H), 7.5 (m, 1H), 3.3 (t, 4H), 2.1 (m, 4H), 1.7 (m, 4H), 1.3-1.2 (m, 8H), 0.8 (m, 4H). 13C NMR (50 MHz, CDCl3): δ 151.9, 140.9, 140.7, 140.2, 128.1, 126.6, 121.8, 120.8, 55.7, 40.9, 34.5, 33.2, 29.6, 28.3, 24.2. GPC (THF, polystyrene standard), Mw: 25,850 g/mol; Mn: 12,840 g/mol; PDI: 2.0. UV-vis (CHCl3): λmax=372 nm; PL (CHCl3): λmax=408 nm.

Example 4-5: Random Copolymer $M_{25}P_{75}$ 2,7-Dibromo-9,9-bis(6'-bromohexyl)fluorene (325 mg, 0.5 mmol), 1,4-phenylenebisboronic acid (62.2 mg, 0.375 mmol), 1,3-phenylenebisboronic acid (20.7 mg, 0.125 mmol), Pd(dppf)Cl$_2$ (7 mg) and potassium carbonate (830 mg, 6 mmol) were placed in a 25 mL round bottle flask. A mixture of water (3 mL) and THF (6 mL) was added to the flask and degassed. The mixture was refluxed at 85° C. for 24 h, and then precipitated into methanol. The polymer was filtered and washed with methanol and acetone, and then dried in vacuum for 24 h to afford $M_{25}P_{75}$ (248 mg, 88%) as an off-white solid. $^1$H NMR (200 MHz, CDCl$_3$): δ 7.9-7.6 (m, 10H), 3.3-3.2 (t, 4H), 2.1 (m, 4H), 1.7-1.6 (m, 4H), 1.3-1.2 (m, 8H), 0.8 (m, 4H). GPC (THF, polystyrene standard), Mw: 29,000 g/mol; Mn: 14,720 g/mol; PDI: 1.9. UV-vis (CHCl$_3$): λmax=365 nm; PL (CHCl$_3$): λmax=407 nm.

Example 4-6: Random Copolymer $M_{50}P_{50}$ 2,7-Dibromo-9,9-bis(6'-bromohexyl)fluorene (325 mg, 0.5 mmol), 1,4-phenylenebisboronic acid (41.5 mg, 0.25 mmol), 1,3-phenylenebisboronic acid (41.5 mg, 0.25 mmol), Pd(dppf)Cl2 (7 mg) and potassium carbonate (830 mg, 6 mmol) were placed in a 25 mL round bottle flask. A mixture of water (3 mL) and THF (6 mL) was added to the flask and degassed. The mixture was refluxed at 85° C. for 24 h, and then precipitated into methanol. The polymer was filtered and washed with methanol and acetone, and then dried in vacuum for 24 h to afford $M_{50}P_{50}$ (220 mg, 78%) as an off-white solid. $^1$H NMR (200 MHz, CDCl$_3$): δ 7.9-7.6 (m, 10H), 3.3-3.2 (t, 4H), 2.1 (m, 4H), 1.7-1.6 (m, 4H), 1.3-1.2 (m, 8H), 0.8 (m, 4H). GPC (THF, polystyrene standard), Mw: 17,340 g/mol; Mn: 10,080 g/mol; PDI: 1.7. UV-vis (CHCl$_3$): λmax=351 nm; PL (CHCl$_3$): λmax=405 nm.

Example 4-7: Random Copolymer $M_{78}P_{25}$ 2,7-Dibromo-9,9-bis(6'-bromohexyl)fluorene (325 mg, 0.5 mmol), 1,4-phenylenebisboronic acid (20.7 mg, 0.125 mmol), 1,3-phenylenebisboronic acid (62.2 mg, 0.375 mmol), Pd(dppf)Cl$_2$ (7 mg) and potassium carbonate (830 mg, 6 mmol) were placed in a 25 mL round bottle flask. A mixture of water (3 mL) and THF (6 mL) was added to the flask. After degassing, the mixture was refluxed at 85° C. for 24 h, and then precipitated into methanol. The polymer was filtered and washed with methanol and acetone, and then dried in vacuum for 24 h to afford $M_{75}P_{25}$ (130 mg, 46%) as an off-white solid. $^1$H NMR (200 MHz, CDCl$_3$): δ 7.9-7.6 (m, 10H), 3.3-3.2 (t, 4H), 2.1 (m, 4H), 1.7-1.6 (m, 4H), 1.3-1.2 (m, 8H), 0.8 (m, 4H). GPC (THF, polystyrene standard), Mw: 13,000 g/mol; Mn: 8,700 g/mol; PDI: 1.4. UV-vis (CHCl3): λmax=342 nm; PL (CHCl$_3$): λmax=400 nm.

Example 4-8: Random Copolymer $M_{90}P_{10}$ 2,7-Dibromo-9,9-bis(6'-bromohexyl)fluorene (325 mg, 0.5 mmol), 1,4-phenylenebisboronic acid (8 mg, 0.05 mmol), 1,3-phenylenebisboronic acid (75 mg, 0.45 mmol), Pd(dppf)Cl$_2$ (7 mg) and potassium carbonate (830 mg, 6 mmol) were placed in a 25 mL round bottle flask. A mixture of water (3 mL) and THF (6 mL) was added to the flask and degassed. The mixture was refluxed at 85° C. for 24 h, and then precipitated into methanol. The polymer was filtered and washed with methanol and acetone and then dried in vacuum for 24 h to afford $M_{90}P_{10}$ (110 mg, 39%) as an off-white solid. $^1$H NMR (200 MHz, CDCl$_3$): δ 7.9-7.6 (m, 10H), 3.3-3.2 (t, 4H), 2.1 (m, 4H), 1.7-1.6 (m, 4H), 1.3-1.2 (m, 8H), 0.8 (m, 4H). GPC (THF, polystyrene standard), Mw: 8,400 g/mol; Mn: 5,800 g/mol; PDI: 1.4. UV-vis (CHCl3): λmax=338 nm; PL (CHCl$_3$): λmax=400 nm.

Example 4-9: Derivatization of Conjugated Polymers

The following procedure may be adapted for use in the derivatization of a conjugated polymer that includes bromo substituted alkyl groups.

Condensed trimethylamine (2 mL) was added dropwise to a solution of the neutral polymer $M_{100}P_0$ (60 mg) in THF (10 mL) at −78° C. The mixture was allowed to warm up to room temperature. The precipitate was re-dissolved by the addition of water (10 mL). After the mixture was cooled down to −78° C., extra trimethylamine (2 mL) was added and the mixture was stirred for 24 h at room temperature. After removing most of the solvent, acetone was added to precipitate $M_{100}P_0$+ (63 mg, 78%) as a light yellow powder. $^1$H NMR (500 MHz, CD$_3$OD): δ 8.1-7.7 (m, 10H), 3.3-3.2 (t, 4H), 3.1 (s, 18H), 2.3 (br, 4H), 1.6 (br, 4H), 1.3 (br, 8H), 0.8 (br, 4H). $^{13}$C NMR (125 MHz, CD$_3$OD): δ 151.9, 142.4, 140.9, 140.6, 129.77, 126.5, 126.1, 125.6, 121.6, 120.5, 66.7, 55.7, 52.5, 40.1, 29.2, 25.8, 23.8, 22.6. UV-vis (H$_2$O): λmax=334 nm; PL (H$_2$O): λmax=369 nm. ε=3.69×10$^4$ M$^{-1}$ cm$^{-1}$ per monomer unit.

Example 4-10

UV-vis and fluorescence spectra for a range of compositions are summarized in Table 3. There is a progressive blue shift in absorption with increasing meta content, consistent with the more effective electronic delocalization across para linkages. The ε values are lowest for polymers with intermediate compositions because the random distribution of conjugated segments results in broader absorption bands.

TABLE 3

Optical properties of polymers of interest.

| $M_nP_m$+ | $\lambda_{max}$, abs | $\lambda_{max}$, em | ε$^a$ | $\Phi_{buffer}$$^b$ |
|---|---|---|---|---|
| $M_{100}P_0$+ | 335 | 369 | 37 | 0.51 |
| $M_{90}P_{10}$+ | 337 | 403 | 32 | 0.57 |
| $M_{75}P_{25}$+ | 347 | 410 | 30 | 0.50 |
| $M_{50}P_{50}$+ | 361 | 421 | 32 | 0.44 |
| $M_{25}P_{75}$+ | 376 | 417 | 42 | 0.42 |
| $M_0P_{100}$+ | 384 | 417 | 46 | 0.42 |

$^a$unit: 10$^3$ Lcm$^{-1}$mol$^{-1}$
$^b$ 50 mmol phosphate buffer, quinine bisulfite as the standard Fluorescence spectra in water as a function of polymer composition. Increasing the para content past the 50:50 ratio does not perturb the emission maxima. Fast energy transfer, either by intra- or interchain mechanisms, localizes excitations on the longest conjugation segments within the lifetime of the excited state. Table 3 shows that there is little variation in the fluorescence quantum yields (ϕ in Table 3).

Equation 1 describes how the FRET rate changes as a function of the donor-acceptor distance (r), the orientation factor (κ), and the overlap integral (J).

$$k_{t(r)} \propto \frac{1}{r^6} \cdot k^2 \cdot J(\lambda) \quad (1)$$

$$J(\lambda) = \int_0^\infty F_D(\lambda)\varepsilon_A(\lambda)\lambda^4 d\lambda$$

Since $M_{50}P_{50}$+ and $M_0P_{100}$+ have similar emission frequencies, the value of J using a common acceptor dye should be nearly identical between the two polymers. The fluorescence lifetimes of the two polymers are similar (400±50 ps). Therefore, differences in FRET efficiencies to a common acceptor chromophore can extract information relevant to the average polymer/acceptor chromophore distance and the orientation of transition moments.

Example 4-11

Figure 2:
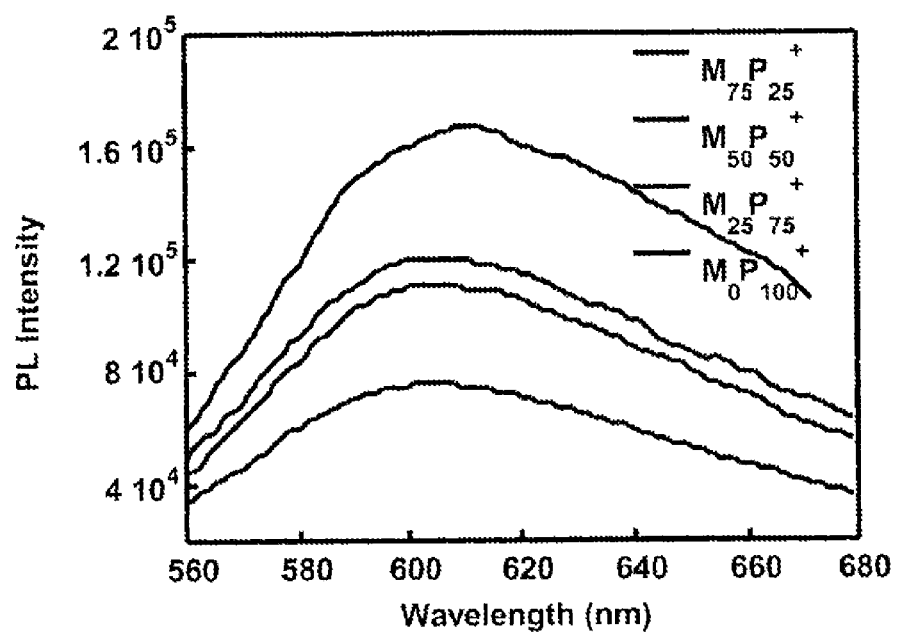
FIG. 2. Comparison of the intensity of signaling chromophore (e.g., EB (EB=Ethidium bromide)) emission from various compositions where a conjugated polymer and a signaling chromophore are connected via a biomolecule, e.g., polymer/ds-DNA/EB in 50 mmol phosphate buffer (pH=7.4) with [ds-DNA]=1.0 $E^{-8}$ M, [Polymer RU]=2.0 $E^{-7}$ M, [EB]=1.1 $E^{-6}$ M. Emission intensity was normalized relative to the E value at the excitation wavelength.

FIG. 2 shoes a comparison of the intensity of signaling chromophore (e.g., EB (EB=Ethidium bromide)) emission from various compositions where a conjugated polymer and a signaling chromophore are connected via a biomolecule, e.g., polymer/ds-DNA/EB in 50 mmol phosphate buffer (pH=7.4) with [ds-DNA]=1.0 E$^{-8}$ M, [Polymer RU]=2.0 E$^{-7}$ M, [EB]=1.1 E$^{-6}$ M. Emission intensity was normalized relative to the E value at the excitation wavelength.

Although the invention has been described in some detail with reference to the preferred embodiments, those of skill in the art will realize, in light of the teachings herein, that certain changes and modifications can be made without departing from the spirit and scope of the invention. Accordingly, the invention is limited only by the claims.

What is claimed is:

1. A composition comprising an aggregate of light harvesting multichromophore conjugated polymers that are configured upon excitation to transfer energy to, and amplify the emission from, an acceptor signaling chromophore in energy-receiving proximity therewith, wherein the light harvesting multichromophore conjugated polymers are linked to a sensor biomolecule that specifically binds a target.

2. The composition according to claim 1, wherein the sensor biomolecule comprising an antibody.

3. The aqueous composition according to claim 1, wherein the multichromophore has a luminescent emission spectrum.

4. The aqueous composition according to claim 1, wherein the conjugated polymers are neutral.

5. The aqueous composition according to claim 1, wherein the multichromophore is linked to a fluorophore.

6. The aqueous composition according to claim 1, wherein the multichromophore is in energy-receiving proximity to an acceptor signaling chromophore.

7. The aqueous composition according to claim 1, wherein the conjugated polymers comprise a conjugated segment having the structure:

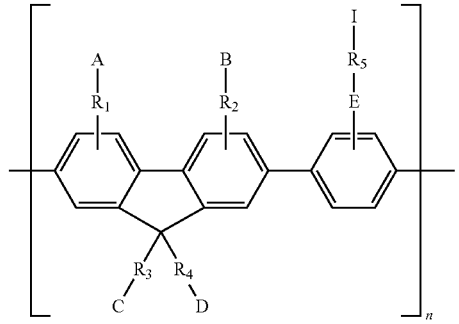

wherein:

$R^1$, $R^2$, $R^3$, $R^4$ and $R^5$ are independently selected from the group consisting of alkyl, alkenyl, alkoxy, alkynyl, and aryl, alkylaryl, arylalkyl, and polyalkylene oxide, each optionally substituted, which may contain one or more heteroatoms, or may be not present;

A, B, C, D and I are independently selected from the group consisting of: hydrogen, —SiR'R"R''', —N+R'R"R''', a guanidinium group, histidine, a polyamine, a pyridinium group, and a sulfonium group;

E is selected from the group consisting of not present, —O—, —S—, —C(O)—, —C(O)O—, —C(R)(R')—, —N(R')—, and —Si(R')(R")—, wherein R' and R" are independently selected from the group consisting of hydrogen, $C_{1-12}$ alkyl and $C_{1-12}$alkoxy and $C_{3-10}$ cycloalkyl; and n is 1 to 10,000.

8. The aqueous composition according to claim 7, wherein $R^3$ and $R^4$ are alkyl, each optionally substituted, which may contain one or more heteroatoms.

9. The aqueous composition according to claim 7, wherein E and $R^5$ are not present.

10. An aqueous labelling composition comprising:
a donor light harvesting multichromophore system comprising an aggregate of conjugated polymers in an aqueous solution that upon excitation are capable of transferring energy to an acceptor signaling chromophore; and
the acceptor signaling chromophore in energy-receiving proximity to the donor light harvesting multichromophore in the aqueous solution;
wherein the donor light harvesting multichromophore system comprises conjugated polymers of aromatic repeat units, wherein the donor light harvesting multichromophore system is directly or indirectly conjugated to the acceptor signaling chromophore.

11. The labelling composition according to claim 10, wherein the acceptor signaling chromophore is a fluorophore.

12. The labelling composition according to claim 10, wherein amplification of the emission from the acceptor signaling chromophore occurs when incident light is at a wavelength absorbed by the donor light harvesting multichromophore system than when the acceptor signaling chromophore is directly excited by incident light.

13. The labelling composition according to claim 12, wherein the amplification of the emission from the acceptor signaling chromophore is 2-fold greater or more.

14. The labelling composition according to claim 10, wherein the ratio of the donor light harvesting multichromophore system to the acceptor signaling chromophore is 1:1.

15. The labelling composition according to claim 10, wherein the donor light harvesting multichromophore system is directly conjugated to the acceptor signaling chromophore.

16. The labelling composition according to claim 10, wherein the donor light harvesting multichromophore system is indirectly conjugated to the acceptor signaling chromophore.

17. The labelling composition according to claim 10, further comprising a sensor biomolecule.

18. The labelling composition according to claim 10, wherein the conjugated polymers comprise a neutral conjugated segment having the structure:

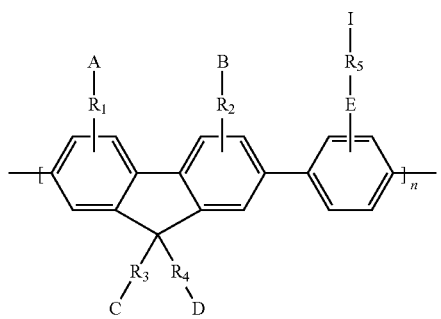

wherein:
$R^1$, $R^2$, $R^3$, $R^4$ and $R^5$ are independently selected from the group consisting of alkyl, alkenyl, alkoxy, alkynyl, and aryl, alkylaryl, arylalkyl, and polyalkylene oxide, each optionally substituted, which may contain one or more heteroatoms, or may be not present;

A, B, C, D and I are independently selected from the group consisting of: hydrogen, —SiR'R"R''', —N+R'R"R''', a guanidinium group, histidine, a polyamine, a pyridinium group, and a sulfonium group;

E is selected from the group consisting of not present, —O—, —S—, —C(O)—, —C(O)O—, —C(R)(R')—, —N(R')—, and —Si(R')(R"), wherein R' and R" are independently selected from the group consisting of hydrogen, $C_{1-12}$ alkyl and $C_{1-12}$alkoxy and $C_{3-10}$ cycloalkyl; and n is 1 to 10,000.

19. An aqueous composition for labelling a target, the composition comprising:
a donor light harvesting multichromophore system comprising an aggregate of conjugated polymers in an aqueous solution that upon excitation are capable of transferring energy to an acceptor signaling chromophore;
the acceptor signaling chromophore in energy-receiving proximity to the donor light harvesting multichromophore in the aqueous solution; and
a sensor biomolecule, wherein the donor light harvesting multichromophore system is directly or indirectly conjugated to the acceptor signaling chromophore.

20. The composition according to claim 19, wherein the acceptor signaling chromophore is a fluorophore.

21. The composition according to claim 19, wherein amplification of the emission from the acceptor signaling chromophore occurs when incident light is at a wavelength absorbed by the donor light harvesting multichromophore system than when the acceptor signaling chromophore is directly excited by incident light.

22. The composition according to claim 19, wherein the amplification of the emission from the acceptor signaling chromophore is 2-fold greater or more.

23. The composition according to claim 19, wherein the ratio of the donor light harvesting multichromophore system to the acceptor signaling chromophore is 1:1.

24. The composition according to claim 19, wherein the donor light harvesting multichromophore system is directly conjugated to the acceptor signaling chromophore.

25. The composition according to claim 19, wherein the conjugated polymers comprise a neutral conjugated segment having the structure:

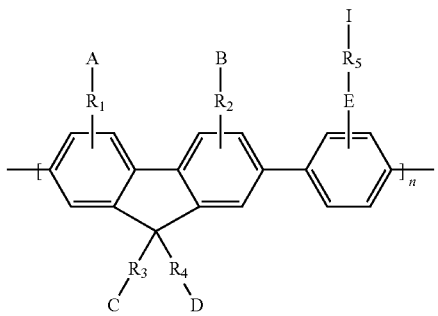

wherein:

$R^1$, $R^2$, $R^3$, $R^4$ and $R^5$ are independently selected from the group consisting of alkyl, alkenyl, alkoxy, alkynyl, and aryl, alkylaryl, arylalkyl, and polyalkylene oxide, each optionally substituted, which may contain one or more heteroatoms, or may be not present;

A, B, C, D and I are independently selected from the group consisting of: hydrogen, —SiR'R"R'", —N+R'R"R'", a guanidinium group, histidine, a polyamine, a pyridinium group, and a sulfonium group;

E is selected from the group consisting of not present, —O—, —S—, —C(O)—, —C(O)O—, —C(R)(R')—, —N(R')—, and —Si(R')(R"), wherein R' and R" are independently selected from the group consisting of hydrogen, $C_{1-12}$ alkyl and $C_{1-12}$ alkoxy and $C_{3-10}$ cycloalkyl; and n is 1 to 10,000.

26. An aqueous composition comprising a light harvesting multichromophore comprising a light harvesting conjugated polymer comprising contributing chromophores that are configured upon excitation to transfer energy to acceptor signaling chromophores in energy-receiving proximity therewith, wherein the light harvesting multichromophore is linked to a sensor biomolecule that specifically binds a target.

27. The composition according to claim 26, wherein the contributing chromophores are fluorenes or substituted fluorenes.

28. The composition according to claim 27, wherein the signaling chromophores comprise a fluorophore.

29. The composition according to claim 28, wherein the fluorophore comprises a BODIPY.

30. The composition according to claim 26, wherein the sensor biomolecule comprising an antibody.

* * * * *

UNITED STATES PATENT AND TRADEMARK OFFICE
CERTIFICATE OF CORRECTION

PATENT NO. : 10,948,485 B2
APPLICATION NO. : 16/802327
DATED : March 16, 2021
INVENTOR(S) : Guillermo C. Bazan et al.

It is certified that error appears in the above-identified patent and that said Letters Patent is hereby corrected as shown below:

On the Title Page

Column 1, Line 23, in item (60), please delete "September 14, 2007" and replace with -- September 12, 2007 --

In the Specification

Column 25, beginning at Line 6, please delete "Conformationally
Flexible CPS
Conjugated polymers (CPS) are efficient light-gathering molecules with properties desirable for a variety of applications. Conjugated polymers can serve as light harvesting materials and signal transducers in fluorescent biosensor applications. These molecules can detect, transduce and/or amplify chemical, biological or physical information into optical and/or electrical signals. CPs can provide the advantage of collective response relative to non-interacting small molecules. This collective response influences optoelectronic properties, such as Förster resonance energy transfer (FRET), electrical conductivity and fluorescence efficiency, properties which can be used to report, or "transduce," target analyte presence."

Signed and Sealed this
Sixth Day of July, 2021

Drew Hirshfeld
*Performing the Functions and Duties of the
Under Secretary of Commerce for Intellectual Property and
Director of the United States Patent and Trademark Office*